US011703818B2

(12) United States Patent
Peters et al.

(10) Patent No.: US 11,703,818 B2
(45) Date of Patent: Jul. 18, 2023

(54) SYSTEMS AND METHODS FOR INDOOR AIR QUALITY BASED ON DYNAMIC PEOPLE MODELING TO SIMULATE OR MONITOR AIRFLOW IMPACT ON PATHOGEN SPREAD IN AN INDOOR SPACE AND TO MODEL AN INDOOR SPACE WITH PATHOGEN KILLING TECHNOLOGY, AND SYSTEMS AND METHODS TO CONTROL ADMINISTRATION OF A PATHOGEN KILLING TECHNOLOGY

(71) Applicant: TRANE INTERNATIONAL INC., Davidson, NC (US)

(72) Inventors: Michael Peters, Mooresville, NC (US); Kaustubh Pradeep Phalak, La Crosse, WI (US); Deep Gupta, La Crosse, WI (US); Gang Wang, Holmen, WI (US); Yi Liu, Concord, NC (US)

(73) Assignee: TRANE INTERNATIONAL INC., Davidson, NC (US)

( * ) Notice: Subject to any disclaimer, the term of this patent is extended or adjusted under 35 U.S.C. 154(b) by 169 days.

(21) Appl. No.: 16/986,083

(22) Filed: Aug. 5, 2020

(65) Prior Publication Data
US 2022/0035326 A1 Feb. 3, 2022

Related U.S. Application Data

(60) Provisional application No. 63/060,487, filed on Aug. 3, 2020.

(51) Int. Cl.
G05B 19/042 (2006.01)
G16H 50/20 (2018.01)
(Continued)

(52) U.S. Cl.
CPC ............. *G05B 19/042* (2013.01); *G06N 7/01* (2023.01); *G06N 20/00* (2019.01); *G06Q 50/06* (2013.01);
(Continued)

(58) Field of Classification Search
CPC .......... G05B 19/042; G05B 2219/2614; G06N 7/005; G06N 20/00; G06Q 50/06;
(Continued)

(56) References Cited

U.S. PATENT DOCUMENTS 5,128,855 A 7/1992 Hilber et al.
5,394,934 A 3/1995 Rein et al.
(Continued)

FOREIGN PATENT DOCUMENTS

WO 2016040954 A2 3/2016
WO 2020/044826 A1 3/2020

OTHER PUBLICATIONS

Office Action issued in U.S. Appl. No. 16/986,086, filed May 11, 2022 (21 pages).
(Continued)

Primary Examiner — Mohammad Ali
Assistant Examiner — Saad M Kabir
(74) Attorney, Agent, or Firm — Hamre, Schumann, Mueller & Larson, P.C.

(57) ABSTRACT

Described herein are heating, ventilation, air conditioning, and refrigeration (HVACR) systems and methods directed to indoor air quality. HVACR systems and methods are based on dynamic people modeling to simulate and/or to monitor airflow impact on pathogen spread in an indoor space. HVACR systems and methods model an indoor space with pathogen killing technology to deploy the pathogen killing technology. HVACR systems and methods are directed to control administration of a pathogen killing technology to an (Continued)

indoor space based on factors that impact airflow including from dynamic analytics, a known input, and/or detection.

16 Claims, 8 Drawing Sheets

(51) Int. Cl.
| | | |
|---|---|---|
| *G16H 50/80* | (2018.01) | |
| *G06Q 50/06* | (2012.01) | |
| *G06Q 50/16* | (2012.01) | |
| *G06N 20/00* | (2019.01) | |
| *G16H 40/67* | (2018.01) | |
| *G06V 20/40* | (2022.01) | |
| *G06V 40/20* | (2022.01) | |
| *G06N 7/01* | (2023.01) | |
| *G16H 15/00* | (2018.01) | |
| *G06Q 10/10* | (2023.01) | |

(52) U.S. Cl.
CPC ........... *G06Q 50/163* (2013.01); *G06V 20/40* (2022.01); *G06V 40/20* (2022.01); *G16H 40/67* (2018.01); *G16H 50/20* (2018.01); *G16H 50/80* (2018.01); *G05B 2219/2614* (2013.01); *G06Q 10/10* (2013.01); *G06V 20/44* (2022.01); *G16H 15/00* (2018.01)

(58) Field of Classification Search
CPC ...... G06Q 50/163; G06Q 10/10; G06V 20/40; G06V 40/20; G06V 20/44; G06V 20/52; G16H 40/67; G16H 50/20; G16H 50/80; G16H 15/00; G16H 40/20; G16H 50/30; G06K 9/0053
USPC ........................................................ 700/276
See application file for complete search history.

(56) References Cited

U.S. PATENT DOCUMENTS

| | | | |
|---|---|---|---|
| 5,597,354 | A | 1/1997 | Janu et al. |
| 5,764,146 | A | 6/1998 | Baldwin et al. |
| 5,971,597 | A | 10/1999 | Baldwin et al. |
| 6,006,142 | A | 12/1999 | Seem et al. |
| 6,298,291 | B1 | 10/2001 | Davis, Jr. et al. |
| 6,406,367 | B1 | 6/2002 | Chou et al. |
| 6,758,739 | B1 | 7/2004 | Sangwan et al. |
| 6,800,022 | B2 | 10/2004 | Urbank et al. |
| 7,044,397 | B2 | 5/2006 | Bartlett et al. |
| 7,266,960 | B2 | 9/2007 | Shah |
| 7,302,313 | B2 | 11/2007 | Sharp et al. |
| 7,596,241 | B2 | 9/2009 | Rittscher et al. |
| 7,801,330 | B2 | 9/2010 | Zhang et al. |
| 8,024,054 | B2 | 9/2011 | Mairs et al. |
| 8,147,302 | B2 | 4/2012 | Desrochers et al. |
| 8,564,661 | B2 | 10/2013 | Lipton et al. |
| 9,383,737 | B2 | 7/2016 | Zaragoza et al. |
| 9,449,514 | B2 | 9/2016 | Schunder et al. |
| 9,593,861 | B1 | 3/2017 | Burnett |
| 9,598,552 | B2 | 3/2017 | Kitago et al. |
| 10,078,787 | B2 | 9/2018 | Carey |
| 10,432,897 | B2 | 10/2019 | Carey |
| 10,458,668 | B2 | 10/2019 | Emmons et al. |
| 10,632,157 | B2 | 4/2020 | Embree et al. |
| 10,636,271 | B2 | 4/2020 | Chang et al. |
| 2005/0144963 | A1 | 7/2005 | Peterson et al. |
| 2005/0156731 | A1 | 7/2005 | Chapman, Jr. et al. |
| 2008/0182506 | A1 | 7/2008 | Jackson et al. |
| 2010/0250009 | A1* | 9/2010 | Lifson .................. F25D 29/003 236/51 |
| 2013/0174646 | A1 | 7/2013 | Martin |
| 2014/0346237 | A1 | 11/2014 | Mirza et al. |
| 2016/0116181 | A1 | 4/2016 | Aultman et al. |
| 2016/0318368 | A1 | 11/2016 | Alger et al. |
| 2017/0157276 | A1 | 6/2017 | Dobrinsky et al. |
| 2018/0001249 | A1 | 1/2018 | Sher |
| 2018/0119973 | A1 | 5/2018 | Rothman et al. |
| 2018/0210413 | A1 | 7/2018 | Frangos |
| 2020/0184153 | A1 | 6/2020 | Bongartz et al. |
| 2020/0393159 | A1 | 12/2020 | Takaya et al. |
| 2021/0011443 | A1 | 1/2021 | McNamara et al. |
| 2021/0313075 | A1 | 10/2021 | McNamara et al. |
| 2021/0390812 | A1 | 12/2021 | Chaurasia et al. |
| 2021/0398691 | A1 | 12/2021 | Dhamija et al. |

OTHER PUBLICATIONS

Christ et al., "Reduced order modelling of flow and mixing in an automobile HVAC system using proper orthogonal decomposition", Applied Thermal Engineering, vol. 133, pp. 211-223, Jan. 9, 2018.

Extended European Search Report, European Patent Application No. 21189234.4, dated Apr. 19, 2022 (9 pages).

Office Action issued in U.S. Appl. No. 16/986,086, filed Feb. 13, 2023 (12 pages).

Office Action issued in U.S. Appl. No. 16/986,086, filed Oct. 26, 2022 (15 pages).

\* cited by examiner

SYSTEMS AND METHODS FOR INDOOR AIR QUALITY BASED ON DYNAMIC PEOPLE MODELING TO SIMULATE OR MONITOR AIRFLOW IMPACT ON PATHOGEN SPREAD IN AN INDOOR SPACE AND TO MODEL AN INDOOR SPACE WITH PATHOGEN KILLING TECHNOLOGY, AND SYSTEMS AND METHODS TO CONTROL ADMINISTRATION OF A PATHOGEN KILLING TECHNOLOGY

FIELD

Described herein are heating, ventilation, air conditioning, and refrigeration (HVACR) systems and methods directed to indoor air quality based on dynamic people modeling to simulate or monitor airflow impact on pathogen spread in an indoor space, and to model an indoor space with pathogen killing technology, and are HVACR systems and methods directed to control administration of a pathogen killing technology to an indoor space based on factors that impact airflow including from dynamic analytics, a known input, and/or detection.

BACKGROUND

Currently the world is experiencing a global pandemic at levels unseen since 1919. Unlike the pandemic in 1919, building owners and operators (commercial, industrial and residential) have different challenges to address the pathogen spread, such as for example more complicated building and space design, an increased populous and densities of people, the increased movement of people worldwide and the general increasing interconnectedness of people worldwide, as well as the technologies associated with accommodating these complications and increases. Building owners and operators turn to building policies, procedures, and operations, and also use technology to kill pathogens and to keep air clean. Further solutions in overcoming such challenges could benefit public health and safety.

SUMMARY

Unlike the pandemic in 1919, building owners and operators (commercial, industrial and residential) have the ability to control conditioned air movement, temperature, humidity and air cleaning technologies within their building. The issue with today's pandemic is that the science around what are best practices to minimize the amount of infection that may occur within the occupied space is still unknown and being studied. Some studies reveal that there may be specific portions of the populace that have proclivity towards higher infection rates and/or higher susceptibility to illness, for example to illness severity of COVID-19.

Described herein are HVACR systems and methods directed to indoor air quality.

In an embodiment, HVACR systems and methods are based on dynamic people modeling to simulate and/or to monitor airflow impact on pathogen spread in an indoor space.

In an embodiment, HVACR systems and methods model an indoor space with pathogen killing technology to deploy the pathogen killing technology.

In an embodiment, HVACR systems and methods are directed to control administration of a pathogen killing technology to an indoor space based on factors that impact airflow including from dynamic analytics, a known input, and/or detection.

An indoor air quality (IAQ) analytics and control system for an HVACR system includes an analytical recognition system having a risk evaluator and a controller. The analytical recognition system is configured to capture and determine behavior parameters for one or more individuals in an indoor space. The risk evaluator is configured to determine a risk assessment based on the behavior parameters. The controller is configured to adjust control parameters of the HVACR system based on the risk assessment.

In an embodiment, an IAQ analytics and simulation system for an HVACR system includes an analytical recognition system and an airflow simulator. The analytical recognition system includes a video camera configured to capture a video sequence of an indoor space, a video analytics module configured to perform video processing and analysis on the video sequence to: identify one or more individuals by processing the video sequence of the indoor space; determine behavior parameters for the one or more individuals based on the video sequence; and generate non-video for each of the behavior parameters. The airflow simulator is configured to simulate an airflow of the indoor space based on the non-video generated by the video analytics module.

A method of analyzing and simulating IAQ for an HVACR system includes obtaining a video sequence of an indoor space by a video camera, and performing video processing and analysis on the video sequence by a video analytics module. Performing video processing and analysis includes identifying one or more individuals by processing the video sequence of the indoor space, determining behavior parameters for the one or more individuals, and generating non-video for each of the behavior parameters based on the video sequence. The method further includes simulating an airflow of the indoor space by an airflow simulator based on the non-video generated by the video analytics module.

An IAQ analytics and control system for an HVACR system includes an analytical recognition system, and a controller. The analytical recognition system includes a video camera configured to capture a video sequence of an indoor space, a video analytics module configured to perform video processing and analysis on the video sequence to: identify one or more individuals by processing the video sequence of the indoor space; determine behavior parameters for the one or more individuals; determine a rate of change for each of the behavior parameters; and generate non-video for the rate of change for each of the behavior parameters. The controller is further configured to determine a risk assessment based on the non-video data. The controller is further configured to adjust control parameters of the HVACR system based on the risk assessment.

In an embodiment, the risk assessment can include input and feedback detection that are not behavior parameters. The input and feedback detection can be used to build indoor air quality systems of building HVACR and lighting controls. The inputs can include for example known information, such as for example genetic and physical markers that can be used to control building temperature, humidity, ventilation, exhaust, control and air cleaning technologies. This can be used for example to control conditioned air spaces and lighting to reduce pathogens or microbiologicals, reduce susceptibility of occupants to infection or reduce impact of illness from pathogens or microbiologicals.

The systems and methods described herein work to solve the lack of input and feedback mechanisms for building control setpoints and operation of buildings (commercial, industrial and residential) for improved health with the presence of microbiological organisms, particulate matter and other airborne substances that may be detrimental to human (or other animal or plant) health. Examples of known information can include but are not limited to genetic markers, age, sex, home address, and past contract tracing of specific people within a building populace to fine tune the humidity, temperature, ventilation rates, exhaust rates and air cleaning mechanisms within the building at an individual level or general population level.

In an embodiment, the systems and methods can be used in concert with sensors to adjust, or in some cases optimize, not just building occupant health but also building energy consumption through demand control indoor air quality mechanisms.

BRIEF DESCRIPTION OF THE DRAWINGS

References are made to the accompanying drawings that form a part of this disclosure and which illustrate the embodiments in which systems and methods described in this specification can be practiced.

DETAILED DESCRIPTION

Figure 1:
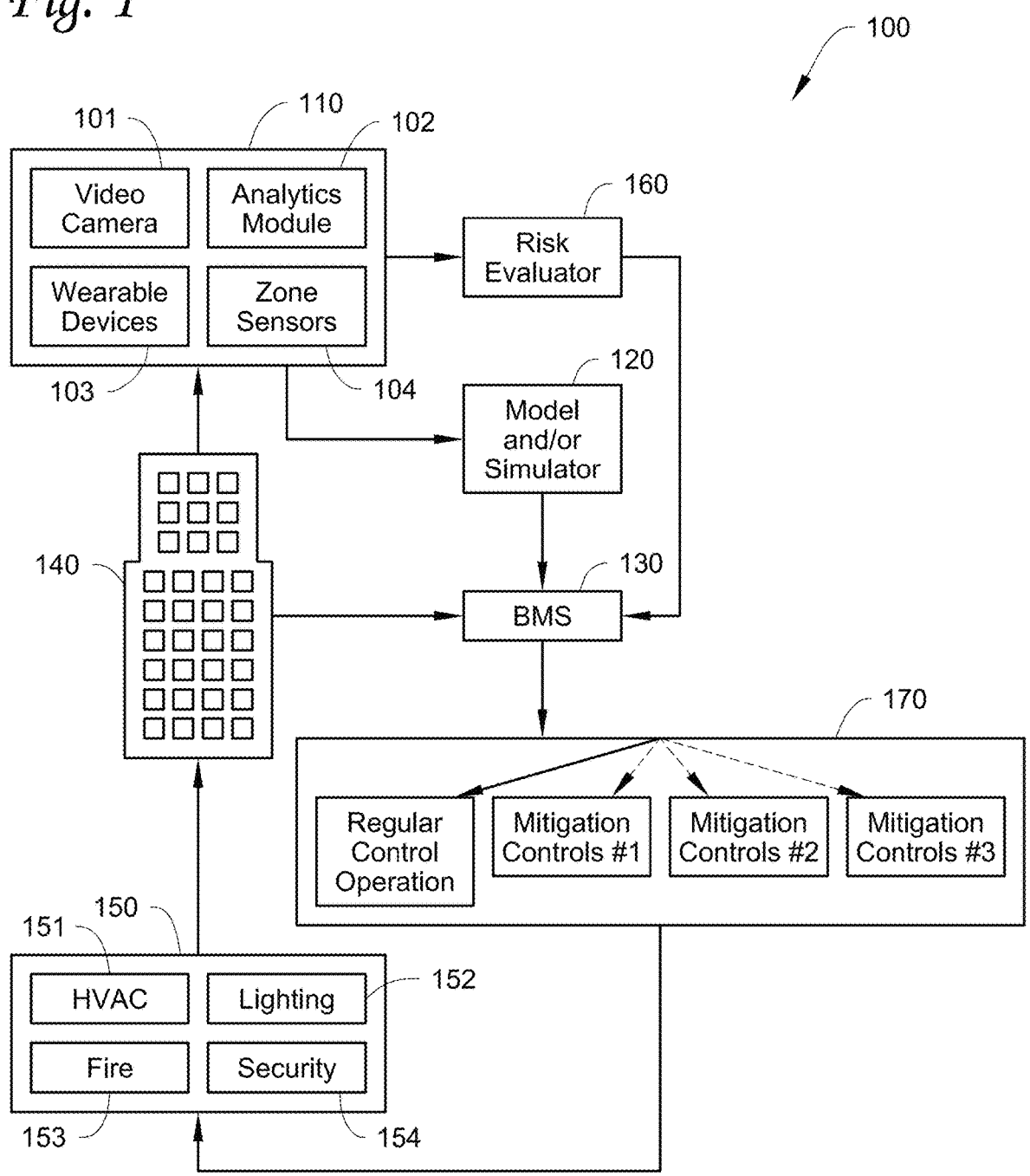
FIG. 1 illustrates a schematic view of an IAQ analytics, simulation, and control system, according to an embodiment.

The following definitions are applicable throughout this disclosure (including above).

As defined herein, the term "video camera" may refer to an apparatus for visual recording. Examples of a video camera may include but are not limited to one or more of the following: a video imager and lens apparatus; a video camera; a digital video camera; a color camera; a monochrome camera; a camera; a camcorder; a PC camera; a webcam; an infrared (IR) video camera (to e.g., capture thermal images and/or create heat map(s), etc.); a low-light video camera; a thermal video camera; a closed-circuit television (CCTV) camera; a pan/tilt/zoom (PTZ) camera; and a video sensing device, and the like. A video camera may be positioned to perform observation of an area of interest.

As defined herein, the term "video" may refer to the motion pictures obtained from a video camera represented in analog and/or digital form. Examples of video may include: television; a movie; an image sequence from a video camera or other observer; an image sequence from a live feed; a computer-generated image sequence; an image sequence from a computer graphics engine; an image sequence from a storage device, such as a computer-readable medium, a digital video disk (DVD), or a high-definition disk (HDD); an image sequence from an IEEE 1394-based interface; an image sequence from a video digitizer; or an image sequence from a network, and the like.

As defined herein, the term "video data" may refer to a visual portion with or without an audio portion of the video, and the like.

As defined herein, the term "non-video data" may refer to non-visual information (e.g., non-video metadata) extracted or generated from the video data, and/or data generated or obtained from other data sources such as a mobile device, a sensor, a wearable device, and the like.

As defined herein, the term "video sequence" may refer to a selected portion of the video data and/or the non-video data, and the like.

As defined herein, the term "video processing" may refer to any manipulation and/or analysis of video data, including, for example, compression, editing, and performing an algorithm that generates non-video data from the video, and the like.

As defined herein, the term "frame" may refer to a particular image or other discrete unit within video, and the like.

As defined herein, the term "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with internet access; a hybrid combination of a computer and an interactive television; a portable computer; a tablet personal computer (PC); a personal digital assistant 123 (PDA); a tablet; a mobile device such as a smart phone or a smart watch; a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system on a chip (SoC), or a multiprocessor system-on-chip (MPSoC); an optical computer; a quantum computer; a biological computer; and an apparatus that may accept data, may process data in accordance with one or more stored software programs, may generate results, and typically may include input, output, storage, arithmetic, logic, and control units; and the like.

As defined herein, the term "software" may refer to prescribed rules to operate a computer. Examples of software may include: software; code segments; instructions; applets; pre-compiled code; compiled code; interpreted code; computer programs; and programmed logic, and the like. In this description, the terms "software" and "code" may be applicable to software, firmware, or a combination of software and firmware, and the like.

As defined herein, the term "computer-readable medium" may refer to any storage device used for storing data accessible by a computer. Examples of a computer-readable medium may include: a magnetic hard disk; a floppy disk; an optical disk, such as a CD-ROM and a DVD; a magnetic tape; a flash removable memory; a memory chip; and/or other types of media that may store machine-readable instructions thereon, and the like. As defined herein, the term "non-transitory" computer-readable medium includes any computer-readable medium, with the sole exception being a transitory, propagating signal, and the like.

As defined herein, the term "computer system" may refer to a system having one or more computers, where each computer may include a computer-readable medium embodying software to operate the computer. Examples of a computer system may include: a distributed computer system for processing information via computer systems linked by a network; two or more computer systems connected together via a network for transmitting and/or receiving information between the computer systems; and one or more apparatuses and/or one or more systems that may accept data, may process data in accordance with one or more stored software programs, may generate results, and typically may include input, output, storage, arithmetic, logic, and control units; and the like.

As defined herein, the term "network" may refer to a number of computers and associated devices that may be connected by communication facilities. A network may involve permanent connections such as cables or temporary connections such as those made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet. Exemplary networks may operate with any of a number of protocols, such as Internet protocol (IP), asynchronous transfer mode (ATM), and/or synchronous optical network (SONET), user datagram protocol (UDP), IEEE 802.x, etc.

As defined herein, the term "real time" or "real-time" analysis or analytics generally refers to processing real time or "live" video and providing near instantaneous reports or warnings of abnormal conditions (pre-programmed conditions), abnormal scenarios (violating the social distancing recommendation, removing face masks, coughing, sneezing, rising body temperature within a predetermined period of time, etc.) or other scenarios based on behavior of elements (customers, employees, people in crowd, etc.) in one or multiple video streams, and the like.

As defined herein, the term "post time" or "post-time" analysis or analytics generally refers to processing stored or saved video from a camera source (from a particular camera system (e.g., store, hospital, building, etc.) or other video data (cell phone, home movie, etc.) and providing reports or warnings of abnormal conditions (post-programmed conditions), abnormal scenarios (violating the social distancing rule, removing face masks, coughing, sneezing, rising body temperature within a predetermined period of time, etc.) or other scenarios based on behavior of elements (customers, employees, people in crowd, etc.) in one or more stored video streams, and the like.

As defined herein, the term "attribute" may refer to behaviors and/or other characteristics of people and/or non-human objects. For example, the "attribute" of a person and/or an object may include e.g., behavior parameters of a person including one or more of a distance between this person and others, a facial direction of the person, an object indicative of mask wearing of the person, an action indicative of mask removing from the person, an action indicative of the person talking to others, a location of the person, a movement of the person, a velocity of the movement of the person, a voice threshold of the person, a body size of the person, a gesture of the person, a gait of the person indicative of the age and/or gender of the person, and/or a body temperature of the person, etc. The "attribute" of a person and/or an object may also include spatial parameters of an object including one or more of a shape of an object, a size of the object, a length of the object, a width of the object, a height of the object, a volume of the object, a profile of the object, a location of the object, a geometry of the object, a gap between objects, and a velocity of a moving object, and the like. The "attribute" of a person and/or an object may further include other types of data associated with the person (e.g., genetic markers, a name, age, sex, a date of birth, a residential address, past contract tracing of the person, and/or the like) or the object, and the like. It will be appreciated that the behavior parameters, the spatial parameters, and/or other types of data associated with the person/object can be captured/obtained from devices such as video cameras, sensors, wearable devices, mobile devices (smart phone, laptop, tablet, etc.), databases, or other data sources, and the like.

As defined herein, the term "indoor air quality" or "IAQ" may refer to the quality of air that is being circulated and/or recirculated inside of a facility (such as a building, an installation, or any suitable enclosed area, etc.) by using, e.g., an HVACR system or the like.

IAQ may be impacted by various factors such as a density of people (and/or objects such as a forklift, etc.) inside the facility, behaviors and/or characteristics of people/objects inside the facility (location, movement paths, velocity of the movement, distance between each other, talking to each other, coughing, sneezing, loudness of the voices, wearing a face mask, removing the face mask, body size, body temperature, facial direction, etc.), airflow paths, whether and/or where and/or how the airflow is disinfected, locations of the vent, humidity and temperature of the airflow, etc.

The density and/or behaviors and/or characteristics of people inside the facility at a predetermined time period (e.g., day time, night time, work day, weekends, etc.) may impact the IAQ. For example, the bacteria, virus, or other pathogens carried or generated by people inside the facility may contaminate the airflow and be spread out through the airflow. The movement and/or breath and/or voice of people inside the facility may impact the direction and velocity of the airflow.

Embodiments disclosed herein can capture the density and/or behaviors and/or characteristics of people inside the facility, analyze the captured data and create attributes for the captured data, simulate an airflow inside the facility based on the attributes, and control the HVACR system and/or other device(s) to adjust the control of the airflow based on the simulated airflow.

With the simulated airflow, critical point(s) and/or path(s) can be determined such that a control of the airflow can be conducted before the airflow reaches the critical point(s) and/or path(s). A critical point and/or path may be reference to a location or path that if the airflow is disinfected or a pathogen killing/reducing material or an anti-pathogen material (that react with bacterial, virus, or other pathogen in the air to kill the pathogen, e.g., the material can be dry hydrogen peroxide, generated by, e.g., a UV lamp excites water molecules on a catalyst) is introduced at/around, before, or after reaching such location or path, the overall IAQ is optimal (e.g., regarding pathogen reducing/killing). In one embodiment, the critical point and/or path is a location or a path where e.g., the social distancing or other rules/recommendations are violated.

The simulation of the airflow may include simulating airflow impacted by the density and/or behaviors and/or characteristics of people inside the facility, simulating airflow with contamination (of bacteria, virus, or other pathogen, etc.), and/or simulating the impact of various pathogen killing mechanisms on the quality of the indoor air. The simulation of the airflow may be based on running a model (pre-created or dynamically generated) that receives the attributes (from the captured density and/or behaviors and/or characteristics of people inside the facility) as input.

The control of the airflow including adjusting operational parameters of the HVACR system (to adjust e.g., the temperature, humidity, direction, velocity, of the airflow, etc.), disinfect the airflow (e.g., by placing/adding pathogen killing device(s) at or around the critical point(s) and/or path(s), increasing or decreasing a material (that can kill/reduce pathogens) introduced to the airflow, activating or deactivating different control zones of the HVACR system, etc.).

Embodiments disclosed herein provide an airflow control based on the simulated airflow, which is in turn based on the density and/or behaviors and/or characteristics of people inside the facility at a given period of time. Embodiments disclosed herein can dynamically adjust (e.g., either real time or post time) the airflow control based on the density and/or behaviors and/or characteristics of people inside the facility, to achieve an optimal IAQ while maintain/reduce the cost of running, e.g., the HVACR system. For example, at night or during weekends, the density of people inside the facility may be at the minimum, and the control of the airflow can be adjusted accordingly (e.g., reducing the solution being added, removing the pathogen killing device(s), deactivate the zone controlled by the HVACR system, etc.).

In an embodiment, any one or more of capturing (e.g., via video camera, wearable device(s), sensor(s), etc.) the density and/or behaviors and/or characteristics of people inside the facility (including the structure and/or layout of the facility), analyzing the captured data to generate attributes corresponding to the captured data, simulating the airflow using the attributes and other data (e.g., the configuration of the HVACR system or other IAQ control devices such as a pathogen killing device) as input, simulating the control of the HVACR system or other IAQ control devices to achieve an optimal IAQ, and actual controlling of the HVACR system or other IAQ control devices to achieve an optimal IAQ can be done post time. In such embodiment, the controlling of the HVACR system or other IAQ control devices to achieve an optimal IAQ is based on past experience and statistics.

In an embodiment, capturing (e.g., via video camera, wearable device(s), sensor(s), etc.) the density and/or behaviors and/or characteristics of people inside the facility (including the structure and/or layout of the facility), analyzing the captured data to generate attributes corresponding to the captured data, simulating the airflow using the attributes and other data (e.g., the configuration of the HVACR system or other IAQ control devices such as a pathogen killing device) as input, simulating the control of the HVACR system or other IAQ control devices to achieve an optimal IAQ, and actual controlling of the HVACR system or other IAQ control devices to achieve an optimal IAQ can be done real time. In such embodiment, the controlling of the HVACR system or other IAQ control devices to achieve an optimal IAQ is conducted in real time based on the dynamic behaviors of the people inside the facility.

Embodiments disclosed herein utilize video analytical recognition system including a video camera for observing and capturing human behaviors with respect to pathways and interactions, and a video analytics module configured to perform video processing and analysis on the video sequence captured by the video camera. The video camera can be used to, e.g., identify a common static pathway used for e.g., initial placement of pathogen killing devices (or adjustment the operational parameters of the HVACR system, etc.) to ensure the safety and well-being of the people involved instead of sending a person out to observe and collect information (which can be based on a larger sample size of data than a human would be capable of collecting). The video camera can also be used to, e.g., capture the changes in pathways due to dynamic situations that effect the people interactions and/or contamination potential by capturing, e.g., people's movement and/or behavior inside a facility.

The video analytical recognition system can work with a Building Management System (BMS) analytics and controls to create a "continuous commissioning" configuration. Combining a model of a building (including an airflow model built with e.g., physics, or machine learning/artificial intelligence algorithms) with a real-time feed of data (from the video analytical recognition system) can provide ever-changing variables/parameters back into the model for use in adjusting building controls (e.g., HVACR controls) for performance, efficiency, and comfort.

Particular embodiments of the present disclosure are described herein with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Additionally, the present disclosure may be described herein in terms of functional block components, code listings, optional selections, page displays, and various processing steps. It should be appreciated that such functional blocks may be realized by any number of hardware and/or software components configured to perform the specified functions. For example, the present disclosure may employ various integrated circuit components, e.g., memory elements, processing elements, logic elements, look-up tables, and the like, which may carry out a variety of functions under the control of one or more microprocessors or other control devices.

Similarly, the software elements of the present disclosure may be implemented with any programming or scripting language such as C, C++, C#, Java, COBOL, assembler, PERL, Python, PHP, or the like, with the various algorithms being implemented with any combination of data structures, objects, processes, routines or other programming elements. The object code created may be executed on a variety of operating systems including, without limitation, Windows®, Macintosh OSX®, iOS®, Linux, and/or Android®.

Further, it should be noted that the present disclosure may employ any number of conventional techniques for data transmission, signaling, data processing, network control, and the like. It should be appreciated that the particular implementations shown and described herein are illustrative of the disclosure and its best mode and are not intended to otherwise limit the scope of the present disclosure in any way. Examples are presented herein which may include sample data items (e.g., names, dates, etc.) which are intended as examples and are not to be construed as limiting. Indeed, for the sake of brevity, conventional data networking, application development and other functional aspects of the systems (and components of the individual operating components of the systems) may not be described in detail herein. Furthermore, the connecting lines shown in the various figures contained herein are intended to represent example functional relationships and/or physical or virtual couplings between the various elements. It should be noted that many alternative or additional functional relationships or physical or virtual connections may be present in a practical electronic data communications system.

As will be appreciated by one of ordinary skill in the art, the present disclosure may be embodied as a method, a data processing system, a device for data processing, and/or a computer program product. Accordingly, the present disclosure may take the form of an entirely software embodiment, an entirely hardware embodiment, or an embodiment combining aspects of both software and hardware. Furthermore, the present disclosure may take the form of a computer program product on a computer-readable storage medium having computer-readable program code means embodied in the storage medium. Any suitable computer-readable storage medium may be utilized, including hard disks, CD-ROM, DVD-ROM, optical storage devices, magnetic storage devices, semiconductor storage devices (e.g., USB thumb drives) and/or the like.

In the discussion contained herein, the terms "user interface element" and/or "button" are understood to be non-limiting, and include other user interface elements such as, without limitation, a hyperlink, clickable image, and the like.

The present disclosure is described below with reference to block diagrams and flowchart illustrations of methods, apparatus (e.g., systems), and computer program products according to various aspects of the disclosure. It will be understood that each functional block of the block diagrams and the flowchart illustrations, and combinations of functional blocks in the block diagrams and flowchart illustrations, respectively, can be implemented by computer program instructions. These computer program instructions may be loaded onto a general-purpose computer, special purpose computer, mobile device or other programmable data processing apparatus to produce a machine, such that the instructions that execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including instruction means that implement the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, functional blocks of the block diagrams and flowchart illustrations support combinations of means for performing the specified functions, combinations of steps for performing the specified functions, and program instruction means for performing the specified functions. It will also be understood that each functional block of the block diagrams and flowchart illustrations, and combinations of functional blocks in the block diagrams and flowchart illustrations, can be implemented by either special purpose hardware-based computer systems that perform the specified functions or steps, or suitable combinations of special purpose hardware and computer instructions.

One skilled in the art will also appreciate that, for security reasons, any databases, systems, or components of the present disclosure may have any combination of databases or components at a single location or at multiple locations, wherein each database or system includes any of various suitable security features, such as firewalls, access codes, encryption, de-encryption, compression, decompression, and/or the like.

The scope of the disclosure should be determined by the appended claims and their legal equivalents, rather than by the examples given herein. For example, the steps recited in any method claims may be executed in any order and are not limited to the order presented in the claims. Moreover, no element is essential to the practice of the disclosure unless specifically described herein as "critical" or "essential."

FIG. 1 illustrates a schematic view of an IAQ analytics, simulation, and control system 100, according to one embodiment. The analytics, simulation, and control system 100 includes an analytical recognition system 110, a model and/or simulator 120, a BMS 130 providing controls 170, a facility 140 having building mechanism systems 150, and a risk evaluator 160. The analytical recognition system 110 includes in some cases one or more video cameras 101 configured to capture a video sequence of an indoor space of the facility 140, in some cases one or more of wearable devices 103, in some cases one or more sensors 104, combinations thereof, and one or more analytics modules 102. In one embodiment, the one or more of wearable devices 103 and/or the one or more sensors 104 may be optional. In one embodiment, the one or more analytics modules 102 may be video analytics modules.

It will be appreciated that the one or more analytics modules 102 and the one or more cameras 101 of the analytical recognition system are disclosed in U.S. Pat. No. 10,432,897, the entire disclosure of which is hereby incorporated by reference herein.

The one or more video cameras 101 can be a network of video and/or data recorders that include the ability to record video. In one embodiment, the one or more video cameras 101 can be e.g., analog and/or IP camera and/or infrared camera. The one or more video cameras 101 can have one or more communication ports, and can connect to a computer having the one or more analytics modules 102 across a connection (e.g., an analog connection and/or a digital connection, wire or wireless) via the one or more communication ports. In another embodiment, the one or more analytics modules 102 are part of the one or more video cameras 101.

The one or more of wearable devices 103 can be a device (e.g., wearable oximeter, pedometer, etc.) that can sense, detect, and/or capture biological signs (temperature, blood pressure, pulse, heart rate, blood oxygenated hemoglobin proportion, movement, etc.) of a person wearing the device inside the facility 140. In one embodiment, the one or more of wearable devices 103 can have one or more communication ports, and can connect to the one or more analytics modules 102 across a connection (e.g., an analog connection and/or a digital connection, wire or wireless) via the one or more communication ports.

The one or more sensors 104 can be a sensor that senses the parameters (temperature, humidity, pressure, sound, light, current and/or voltage, the existence and/or amount of virus at a particular location, etc.) of the facility 140 and/or a person. In one embodiment, the one or more sensors 104 can have one or more communication ports, and can connect to the one or more analytics modules 102 across a connection (e.g., an analog connection and/or a digital connection, wire or wireless) via the one or more communication ports.

The one or more communication ports may be any one or a combination of various types of communication ports. Example types of the one or more communication ports include a WiFi® (a family of wireless network protocols) communication port, a media access control (MAC) communication port, a® (a wireless technology standard) communication port, a cellular communication port, a near field communication port, a radio frequency identification (RFID) communication port, and/or a global positioning system (GPS) communication port, etc.

As discussed in more detail herein, the one or more communication ports are configured to capture mobile communication device data from one or more mobile communication devices (e.g., smartphones) located within a range of the one or more communication ports and transmit the captured mobile communication device data to the analytics module 102 for processing in accordance with various example embodiments herein. The one or more communication ports may be configured to capture the mobile communication device data by wirelessly receiving data transmitted by a mobile communication device that is located within a range of the one or more communication ports. The one or more communication ports may be configured to wirelessly receive data from nearby mobile communication devices by periodically or continually pinging mobile communication devices and/or by being configured to periodically or continually listen for and capture data transmitted by nearby mobile communication devices without using pinging.

The one or more analytics modules 102 may reside in a computer and/or in one or more of the video cameras 101. The one or more analytics modules 102 perform processing of the video and/or the mobile communication device data. For instance, one or more analytics modules 102 perform one or more algorithms to generate non-video data from video and/or from the mobile communication data. Non-video data includes non-video frame data that describes content of individual frames such as, for example, objects identified in a frame, one or more properties of objects identified in a frame and one or more properties related to a pre-defined portions of a frame. Non-video data may also include non-video temporal data that describes temporal content between two or more frames. Non-video temporal data may be generated from video and/or the non-video frame data. Non-video temporal data includes temporal data such as temporal properties of an object identified in two or more frames and a temporal property of one or more pre-defined portions of two or more frames. Non-video frame data may include a count of objects identified (e.g., objects may include people and/or any portion thereof, inanimate objects, animals, vehicles or a user defined and/or developed object) and one or more object properties (e.g., position of an object, position of any portion of an object, dimensional properties of an object, dimensional properties of portions and/or identified features of an object) and relationship properties (e.g., a first object position with respect to a second object), or any other object that may be identified in a frame. Objects may be identified as objects that appear in video or objects that have been removed from video. Objects may be identified as virtual objects that do not actually appear in video but which may be added for investigative purposes, training purposes, or other purposes. The non-video fame data, non-video temporal data, and/or other non-video data can be referred to as non-video metadata of the video.

In various example embodiments herein, the one or more analytics modules 102 are configured to correlate video data and/or mobile communication device data captured by video cameras and the one or more communication ports, respectively, to generate a profile of a person associated with the video data and the mobile communication device data. The profile may include profile data, such as the captured video data, the captured mobile communication data, and/or other types of data associated with the person (e.g., a name, a date of birth, a residential address, and/or the like).

The profile may include captured video data, captured mobile communication device data, temporal data associated with captured video or mobile communication device data, and/or location data associated with the captured video or mobile communication device data. The captured video data may include a captured still image and/or captured video footage. The mobile communication device data may include a Wi-Fi® (a family of wireless network protocols) identifier, a media access control (MAC) identifier, a® (a wireless technology standard) identifier, a cellular identifier, a near field communication identifier, and a radio frequency identifier and/or any other identifier or data associated with a mobile communication device in communication with the communication port. The temporal data may include a time at which corresponding video data is captured and/or a time at which corresponding mobile communication device data is captured. The location data may include a location at which video data is captured and/or a location at which mobile communication device data is captured.

The one or more analytics modules 102 may be configured to add to the profile, based on correlated video data and mobile communication device data, a number of visits of the person to the facility 140 and/or a frequency of visits of the person to the facility 140. The one or more analytics modules 102 may also be configured to compare data obtained from a first source (e.g., a non-government database, a government database, and/or one or more previously generated profiles) to the captured video data, the captured mobile communication device data, the correlated video and mobile communication device data, and/or the profile, and identify the person based on the comparison.

The one or more analytics modules 102 may also be configured to determine, based on the captured video and/or mobile communication device data, an arrival time and/or a departure time of the person at the facility 140. The one or more analytics modules 102 may correlate the video data and/or the mobile communication device data based on the arrival time and/or the departure time. This time-based correlation, for instance, may enable the one or more analytics modules 102 to associate a particular item of mobile communication device data (e.g., a Wi-Fi identifier) with a particular person captured on video.

In one example, the one or more video cameras 101 may be configured to capture multiple sets of video data, respectively. Likewise, the one or more communication ports may be configured to capture multiple sets of mobile communication device data, respectively. The one or more analytics modules 102 may also be configured to correlate the multiple sets of video data and/or mobile communication device data to generate respective profiles for multiple people who are associated with the respective video data and mobile communication device data. The video cameras and the communication ports may be located at a plurality of different locations and/or premises.

In one example, the one or more analytics modules 102 may be configured to determine that the video data, the mobile communication device data, and/or the profile corresponds to an employee or to a person on a predetermined list of people.

In some example embodiments herein, the one or more analytics modules 102 may be configured to detect a behavior of the person and store in the profile behavioral data corresponding to the behavior. The one or more analytics modules 102 may, for instance, be configured to detect the behavior of the person by extracting behavioral information from the video data and/or the mobile communication device data. The behavior (behavior parameters) of the person may include a distance between this person and others, a facial direction of the person, an object indicative of mask wearing of the person, an action indicative of mask removing from the person, an action indicative of the person talking to others, a location of the person, a movement of the person, a velocity of the movement of the person, a voice threshold of the person, a body size of the person, a gesture of the person, a gait of the person indicative of the age and/or gender of the person, and/or a body temperature of the person. The one or more analytics modules 102 may further be configured to classify the person as an employee of the facility 140, a customer of the facility 140 (e.g., a patient of a hospital, etc.), based on facility visit data stored in the profile. The one or more analytics modules 102 may add to the profile, or update in the profile, an indicator of whether the person is a customer of the facility 140. The one or more analytics modules 102, in some cases, may be configured to detect the behavior of the person by correlating the video data, the mobile communication device data, and/or the profile data with a mapping of aisle locations at the facility 140, etc.

In some example aspects herein, the one or more analytics modules 102 may be configured to generate, based on captured video and/or mobile communication device data, location data corresponding to the particular behavior, and store the location data in the profile in association with the corresponding behavioral data.

The one or more analytics modules 102 may be positioned in camera 101 to convert video-to-video data and/or non-video data and to provide the video data and/or the non-video data to a computer. In another embodiment, the one or more analytics modules 102 may be positioned in the computer. The computer includes computer-readable medium comprising software for monitoring user behavior, which software, when executed by the computer, causes the computer to perform operations. A user behavior is defined by an action, an inaction, a movement, a plurality of event occurrences, a temporal event, an externally generated event, or any combination thereof. A particular user behavior is defined and provided to the one or more analytics modules 102.

An action may include putting up an object (e.g., a face mask, a face visor, a face goggle, etc.) around the face area and/or removing such object from the face area. An action may include moving away from or towards others to keep a distance (e.g., a predetermined social distance) between the person and others or to violate the social distance recommendation. An action may include turning face away from or towards face(s) of others. An action may also include moving away from or moving towards others (e.g., at a velocity). An action may also include talking to others, coughing, and/or sneezing. Various other examples of action have been discussed hereinabove.

Inaction may include failing to moving away from others when a distance (e.g., a predetermined social distance) cannot be maintained. Inaction may also include failing to turning face away from others when others are e.g., coughing, or sneezing. Various other examples of inaction have been discussed hereinabove.

A temporal event may include an individual remaining in a particular location for a time period exceeding a threshold. A temporal event may also include an individual staying with other(s) within a distance less than a predetermined distance for time period exceeding a threshold. Various other examples of a temporal event have been discussed hereinabove.

A user may identify a particular user behavior and provide and/or define characteristics of the particular user behavior in the one or more analytics modules 102. The one or more analytics modules 102 generate non-video data from videos from the camera 101 wherein the non-video data includes behavioral information data. The particular user behavior may be defined by a behavior model (e.g., from a library or a database) including one or more attribute such a size, shape, length, width, aspect ratio or any other suitable identifying or identifiable attribute (e.g., face mask or other various examples discussed herein). The one or more analytics modules 102 includes a matching algorithm or matching module, such as a comparator, that compares the defined characteristics and/or the behavior model with user behavior in the defined non-video data. Indication of a match by the matching algorithm or module generates non-video data wherein the non-video data (such as non-video metadata) includes the non-video data identified by the matching algorithm. The non-video metadata are a collection of data related to an identified event, and generally document behaviors of interest. As such, the non-video metadata require further review to understand the particular behavior.

Matching algorithm may be configured as an independent module or incorporated into the one or more analytics modules 102 in the computer or in any cameras 101. The one or more analytics modules 102 may also include a comparator module configured to compare the behavior model of the particular user behavior and the non-video data.

Comparing the behavior model and the non-video data can be based on pre-programmed parameters, e.g., real time and post time analysis, recognition, tracking of various pre-programmed (or post programmed) known objects or manually programmed objects based on parameters (e.g., behavior parameters such as shape, color, size, distance between/among person(s), face masks, facial direction, voice, gait, gesture, etc.). Programmed objects may include objects with a particular known shape, size color or weight or based upon a look up library or database of objects and mapping algorithm. These objects may be pre-programmed into the analytical software and tracked in real time and/or post time for analysis. Manually programmed objects may be inputted into the software by color, size, shape, weight, etc. and analyzed and tracked in real time and/or post time to determine abnormal conditions or for other purposes. Manually programmed objects may be uploaded for analysis in real time, e.g., facial recognition images, or other indicia. Additionally, a user generated item and/or image may be generated from video data (e.g., frame data) and/or a still image and provided for analytics.

For example, a particular user behavior may be defined as a person getting closer to another person such that the distance between them is less than a predetermined distance. This particular user behavior is indicative of a person violating a social distancing rule or recommendation. The one or more analytics modules 102 performs an algorithm to generate non-video data that identifies the distance of individuals and/or the time and/or the location of the occurrence. The one or more analytics modules 102 may also provide a vector indicating the facial and/or eye direction. The matching algorithm searches the non-video data to determine if the distance indicating social distance exceeds the preset distance. A match results in the generation of a flag along with the non-video data.

The person captured or identified in the video may possess a mobile communication device (e.g., a smartphone) by which one or more signals (e.g., mobile communication device data) are wirelessly transmitted. Examples of such mobile communication device data include signals (e.g., handshaking signals, data such as person's age, blood type, body temperature or changes of body temperature, density of people, etc. from an app such as a COVID tracking system, etc.) that the mobile communication device transmits in accordance with one or more wireless communication protocols, such as a Wi-Fi® (a family of wireless network protocols) communication protocol, a media access control (MAC)-based communication protocol, a® (a wireless technology standard) protocol, a cellular protocol, a near field communication protocol, and a radio frequency identification protocol. As discussed above, the one or more communication ports (e.g., of the video camera 101) are configured to capture the mobile communication device data transmitted by the mobile communication device when it is located within a range of the one or more communication ports and transmit the captured mobile communication device data to the one or more analytics module 102 for processing in accordance with various example embodiments herein.

The one or more analytics module 102 is configured to perform real time and/or post time analysis of video and non-video data (e.g., mobile communication device data) and tracking of every person within a particular area or within a particular camera view in an indoor space of the facility 140. Behavior of interest of one or more persons may be tracked and recorded and analyzed in either real time or post time. For example, if a group of people gathered in a space violating the social distancing rule/recommendation, this video may be flagged for real time alerts (in addition to the non-video data such as data for behavior parameters generated from the video) and/or post time analysis. The objects, e.g., the group of person, the location, etc., might be flagged, time stamped and/or separated into an individual video stream for analysis later. A user in real time or post time analysis can zoom in for high-definition tracking. The person removing the face mask (or any other object that is recognized by a library of images, user generated image/object (via an input device) or a certain mapping algorithm or module 102) may be tracked and analyzed for real time alerts (in addition to the non-video data generated from the video) and/or post time analysis.

The system 110 may both track the object and flag and track the person for real time or post time analysis through one or more cameras 101, one or more wearable devices 103, one or more sensors 104, etc. In another example, the system 110 may flag and track in real time for alert purposes (in addition to the non-video data generated from the video) or post time analysis a person having an abnormal high temperature and/or coughing continuously, etc. This would also be classified as an alert or abnormal condition.

The system 110 may be capable of combining pre-programmed analytics to alert for one or more (or a combination of) abnormal scenarios. For example, a person coughing continuously and that person walking toward another person within a predetermined distance may be automatically flagged, tracked and an alert (in addition to the non-video data generated from the video) sent to the system 110.

The one or more analytics module 102 may also utilize gait as an indicator of an individual, which includes limp, shuffle, head angle, stride, hand sway, hand gestures, etc. A person's gait is as individual as a fingerprint and may be used to identify e.g., a person's age. Many variables contribute to an individual gait and this information can be uploaded to the one or more analytics module 102 (e.g., walk velocity, step frequency, angle between feet, hand/arm position, hand/arm sway, limp, shuffle, etc.).

In another example, the one or more analytics module 102 may be configured to perform real-time video processing and analysis to determine a behavior parameter (e.g., a real-time crowd count, a real-time crowd density estimation, etc.) by automated processing of the video sequence of a physical indoor space. The one or more analytics module 102 may include one or more algorithms configured to determine a rate of change in the behavior parameter. The rate of change in the behavior parameter may be indicative of crowd convergence or crowd divergence.

When the rate of change in the behavior parameter exceeds a predetermined threshold, the one or more analytics module 102 automatically issues an alert. For example, when the rate of change in the behavior parameter is indicative of crowd convergence and the number of people exceeds a predetermined threshold (e.g., more than 250 people gathered in an indoor space, which might be a violation of social distancing rule/recommendation regarding a bar), the one or more analytics module 102 may raise an alert/flag in addition to the non-video data (e.g., non-video metadata) of the behavior parameters generated from the video. In one embodiment, the one or more analytics module 102 may also provide a vector indicating behavior parameters such as the facial and/or eye direction, etc. The one or more analytics module 102 may be configured to utilize vector analysis and/or image and data vector analysis algorithms and/or machine learning algorithms to assess one or more convergence patterns.

The one or more analytics module 102 may be configured to analyze data received from the one or more cameras 101, the one or more of wearable devices 103, the one or more sensors 104, and/or other devices such as mobile communication devices, and generate attributes from the received data. The one or more cameras 101, the one or more of wearable devices 103, and/or the one or more sensors 104 are configured to capture/sense/obtain/determine data (e.g., behavior parameters, etc.) of person(s) or other objects in the facility 140.

In one embodiment, the attributes (e.g., non-video data indicative of the behavior parameters or a rate of change to each of the behavior parameters) generated by the one or more analytics module 102 can be sent (e.g., via a wire or wireless communication) to the simulator 120. The rate of change for each of the behavior parameter is a change of the behavior parameter over a predetermined period of time.

The simulator 120 can include an airflow simulator and/or a control simulator (e.g., simulate the energy efficiency of different control of e.g., an HVACR system). The simulator 120 can be configured to simulate an airflow of the indoor space based on the non-video data generated by the one or more analytics modules 102. The simulator 120 can be configured to create an airflow model using the non-video data as input, simulate the airflow in the indoor space, and/or determine a critical point and/or critical path based on the simulated airflow. The simulator 120 can obtain data (such as where air comes in, where air comes out, air velocities, airflow, equipment (e.g., of an HVACR, lighting, fire, or security system, etc.) in the building, layout of the building, 3D modelling of the data), together with the non-video data (such as the behavior parameters and changes of the parameters overtime, parameters and changes of the parameters of an object such as a forklift, etc.), and simulate where the airflow exists within the space. In one embodiment, the 3D model created/obtained for simulation can be, a dynamic model based on a static figuration (i.e., without the non-video data). The non-video data can represent dynamic flow (e.g., airflow) of the facility and be added into the 3D model to predict when (e.g., daytime, night, workday, weekends, etc.) and where critical point(s)/path(s) of the airflow exists.

A critical point and/or path may be referring to a location or path that if the airflow is disinfected or a pathogen killing material is introduced at/around, before, or after reaching such location or path, the overall IAQ is optimal (e.g., regarding pathogen reducing/killing). In one embodiment, the critical point and/or path is a location or a path where e.g., the social distancing or other rules/recommendations are violated.

The determined critical point/path from the simulator 120 can be sent (e.g., via a wire or wireless communication) to the BMS for further processing (e.g., provide controls 170 for the building mechanism systems 150). If no critical point/path is determined (i.e., there is no violation to e.g., the social distancing or other rules/recommendations), the BMS 130 (e.g., a process or a controller of the BMS, a controller of the HVACR system, etc.) is configured to operate the building mechanism systems 150 with a predetermined configuration (e.g., regular control operation having predetermined setpoints of temperature, humidity, zone control, pathogen killing material, etc.). The building mechanism systems 150 includes an HVACR system 151, a lighting system 152, a fire system 153, and/or a security system 154, etc. The building mechanism systems 150 is disposed in the facility 140. The BMS 130 can obtain/monitor different parameters in the building (e.g., via sensors, transducers, etc. of the BMS 130), and perform corresponding control operations through the building mechanism systems 150 based on the obtained parameters.

If one or more critical point/path is determined, depending on the location of the critical point/path and other parameters (e.g., severity of the critical point/path, layout of the building mechanism systems 150, etc.), the BMS 130 is configured to operate the building mechanism systems 150 with configurations having different mitigation controls. For example, one mitigation control can be adjusting a control of the HVACR system 151 on the airflow before the airflow reaches the critical point. In another embodiment, one mitigation control can be placing a pathogen killing device (e.g., of the HVACR system 151) in the indoor space at or around the critical point. In yet another embodiment, one mitigation control can be activating or deactivating control of a zone of the HVACR system 151 within the indoor space upstream of the critical point relative to a direction of the airflow. In yet another embodiment, one mitigation control can be increasing or decreasing a pathogen killing material in the airflow of the HVACR system 151 upstream of the critical point relative to a direction of the airflow. Different mitigation control can reduce the risk for a specific parameter (e.g., spread of virus, etc.) or achieve an optimal configuration for risk assessment (that includes e.g., a risk index ranging from 0 to 1) of multiple parameters (e.g., in a weighted fashion for different zone, etc.).

It will be appreciated that the BMS 130 (or building automation system) is disclosed in U.S. Pat. Nos. 9,383,737 and 8,024,054, the entire disclosure of which are hereby incorporated by reference herein.

It will also be appreciated that the determined critical point/path from the simulator 120 can be sent (e.g., via a wire or wireless communication) to the BMS for setting up, deploying, and/or configuring e.g., the layout of the building mechanism systems 150.

In another embodiment, instead of the simulator 120, the system 100 includes a risk evaluator 160. The risk evaluator 160 is configured to receive data from the system 110, analyze and/or assess the data, and determine a risk index based on the received data.

It will be appreciated that one or more of the video processing and analysis on the video sequence, simulating the airflow of the indoor space based on the non-video data, determining the risk assessment, and adjusting the control parameters of the HVACR system can be performed in real-time. For example, adjusting the control parameters of the HVACR system can be performed in real-time in response to the current airflow in the facility. In another embodiment, deployment of analytics tools (such as the video cameras 101, the wearable devices 103, and/or the sensors 104 of the system 110) may be a temporary installation into the facility, for e.g., a period of predetermined time (e.g., two weeks) to observe the operation of the facility and generate data (airflow and/or critical point/path of the airflow, etc.) for analytics.

It will be appreciated that any of the modules (e.g., structures, functions, configurations, and/or arrangements) in FIG. 1 can work independently or combined with one or more of other modules. For example, the system 110 can (1) work independently, (2) work with the risk evaluator 160 to determine a risk assessment based on the outputs from the system 110, (3) work with the risk evaluator 160 and the BMS 130 to determine a risk assessment and adjust the controls (of e.g., the HVACR system 151) based on the risk assessment, (4) work with the simulator 120 to create a model and/or to perform simulation based on the outputs from the system 100, or (5) work with the simulator 120 and the BMS 130 to create a model or perform a simulation and adjust the controls (of e.g., the HVACR system 151) based on the model or the simulation. Similarly, the risk evaluator 160 can (1) work independently, or (2) work with the BMS 130 to adjust the controls (of e.g., the HVACR system 151) based on a risk assessment from the risk evaluator 160. The simulator 120 can (1) work independently to create a model and/or to perform simulation, or (2) work with the BMS 130 to adjust the controls (of e.g., the HVACR system 151) based on the model or the simulation.

Figure 2:
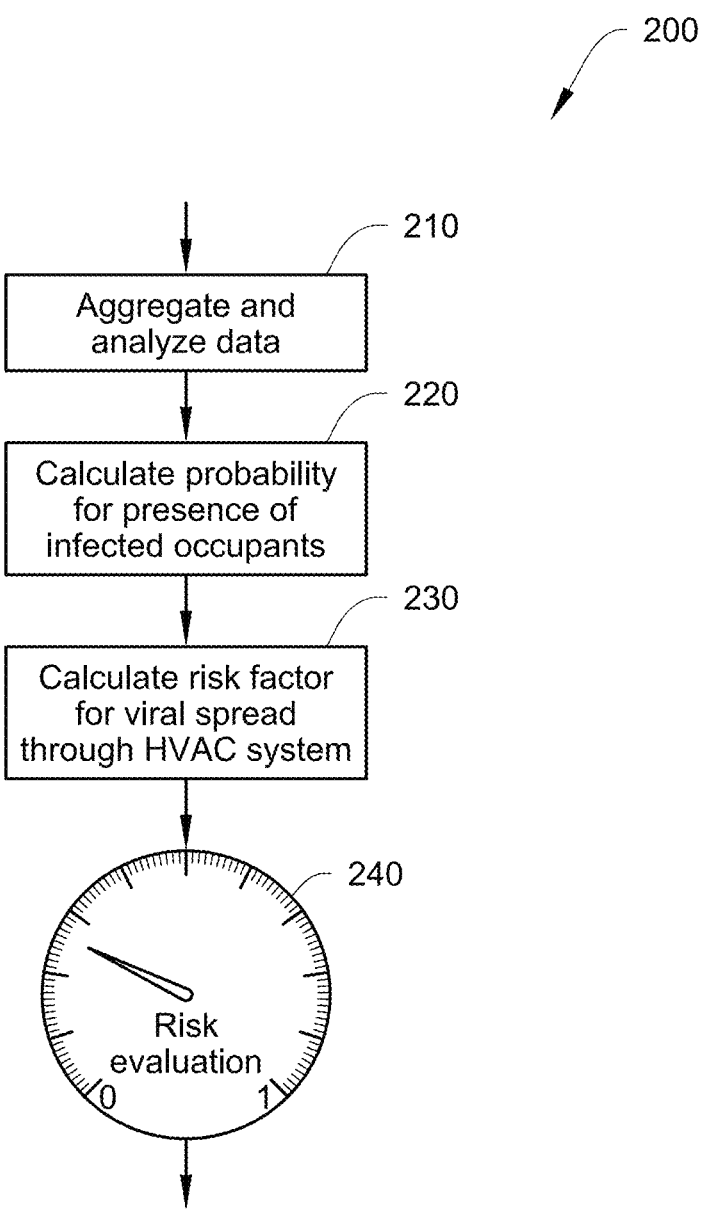
FIG. 2 illustrates a flow chart of controls of a risk evaluator of an IAQ analytics, simulation, and control system, according to an embodiment.

FIG. 2 illustrates a flow chart 200 of controls of a risk evaluator 160 of an IAQ analytics, simulation, and control system, according to one embodiment. The flow chart 200 starts from 210. At 210, the risk evaluator 160 receives data from the system 110 of FIG. 1, aggregate and analyze the received data. The data can be the video data or non-video data from the video camera 101 and/or the analytics module 102, biological signs (temperature, blood pressure, pulse, heart rate, blood oxygenated hemoglobin proportion, movement, etc.) of a person wearing the device 103 inside the facility 140, and/or sensed parameters (temperature, humidity, pressure, sound, light, current and/or voltage, etc.) of the facility 140 and/or a person from the sensor 102. Then the flow chart proceeds to 220.

At 220, the risk evaluator 160 calculates/determines a probability for presence of particular individual(s) (e.g., occupant(s) infected by the infectious disease) based on the aggregated/analyzed data from 210. Then the flow chart proceeds to 230.

At 230, the risk evaluator 160 calculates/determines risk factor(s) for e.g., viral spread through the HVACR system 151, based on the probability from 220. Then the flow chart proceeds to 240.

At 240, the risk evaluator 160 calculates/determines a risk assessment (represented by, e.g., integers from 1 to 10 or from 1 to 100, or a number between 0 and 1). The risk assessment can be used to determine e.g., whether/which mitigation control is to be configured for the HVACR system 151.

Figure 3:
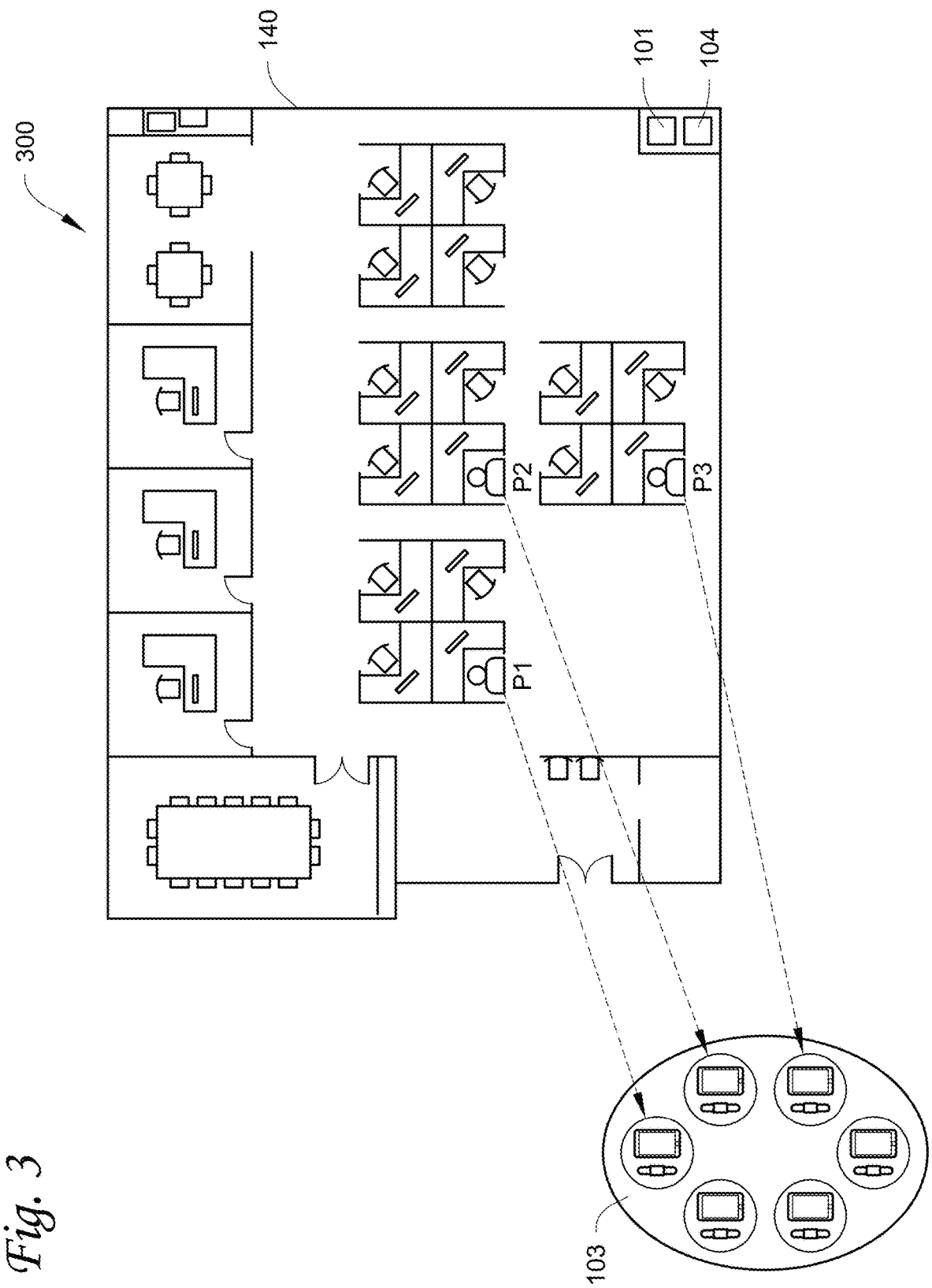
FIG. 3 illustrates a schematic view of an indoor space of a facility, according to an embodiment.

FIG. 3 illustrates a schematic view of an indoor space 300 of a facility 140, according to one embodiment. As shown in FIG. 3, a group of people (P1, P2, and P3) are in the indoor space 300 of the facility 140 of FIG. 1. Each person wears one or more wearable devices 103. One or more video cameras 101 are disposed in the indoor space 300 (at various suitable locations that can capture e.g., the behavior parameters of the group of people). The one or more sensors 104 (e.g., zone sensors including zone microphones, etc.) are disposed in the indoor space 300 (at various suitable locations that can capture sensed data of the group of people and/or the indoor space 300).

Figure 4:
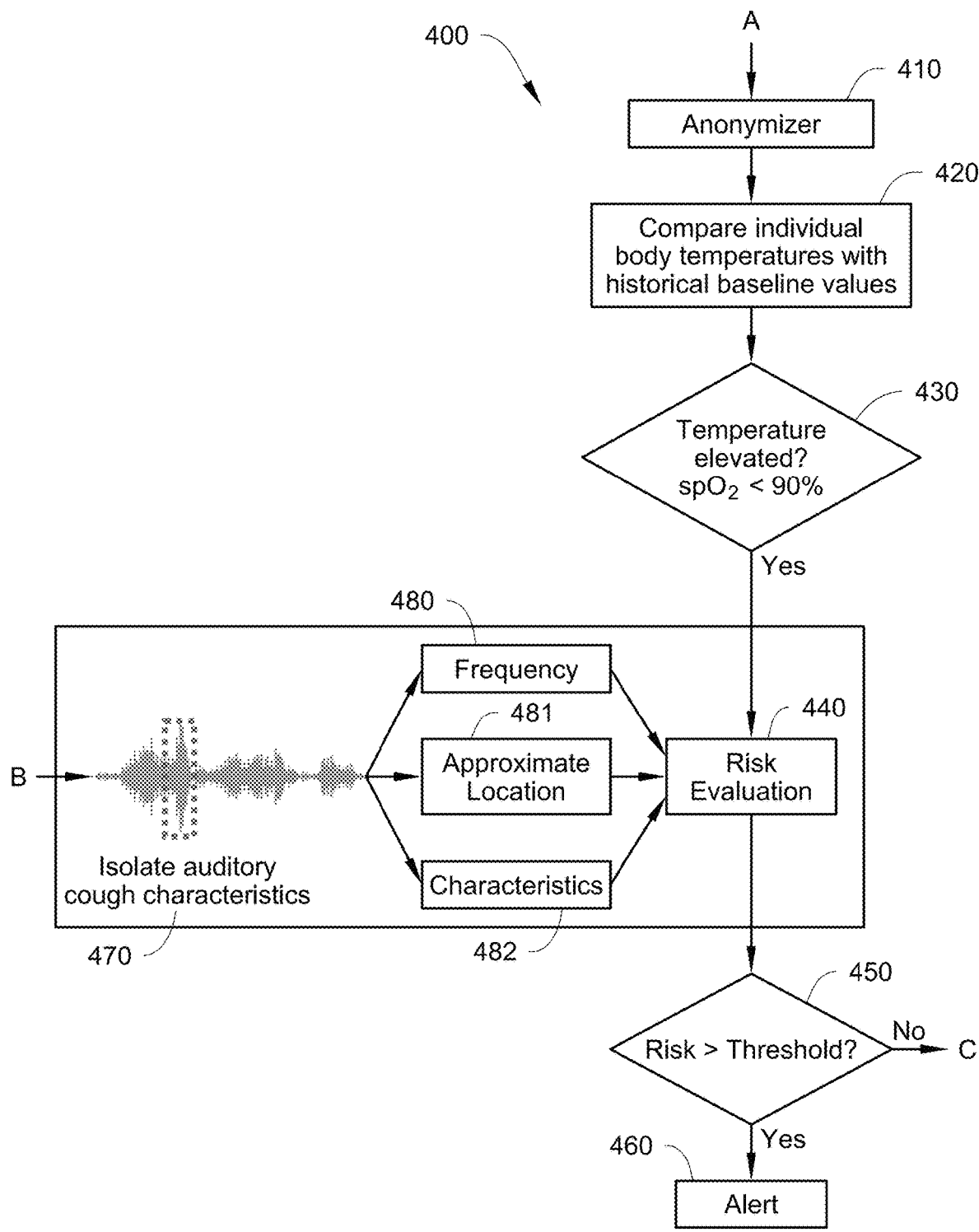
FIG. 4 illustrates a flow chart of controls of a risk evaluator of an IAQ analytics, simulation, and control system, according to an embodiment.

FIG. 4 illustrates a flow chart 400 of controls of a risk evaluator 160 of an IAQ analytics, simulation, and control system, according to one embodiment. The flow chart 400 starts from 410. At 410, the risk evaluator 160 receives data from A (e.g., the one or more wearable devices 103), and an anonymizer of the risk evaluator 160 is configured to remove personal information (e.g., HIPAA info under the Health Insurance Portability and Accountability Act) from the received data. Then the flow chart proceeds to 420.

At 420, the risk evaluator 160 compares individual data (e.g., individual body temperature) from 410 with historically baseline value (which can be predetermined). Then the flow chart proceeds to 430.

At 430, the risk evaluator 160 determines, based on the comparison from 420, whether the comparison exceeds a predetermined threshold. For example, whether the body temperature data received is elevated over a predetermined period of time, whether SpO2 is less than 90%. It will be appreciated that SpO2, also known as oxygen saturation, is a measure of the amount of oxygen-carrying hemoglobin in the blood relative to the amount of hemoglobin not carrying oxygen. It will be appreciated that the body needs there to be a certain level of oxygen in the blood to function as efficiently. Oxygen saturation is the fraction of oxygen-saturated hemoglobin relative to total hemoglobin in the blood. The human body requires and regulates a very precise and specific balance of oxygen in the blood. Normal arterial blood oxygen saturation levels in humans are 95-100 percent. Then the flow chart proceeds to 440.

The flow chart 400 can also start from 470. At 470, the risk evaluator 160 receives data from B (e.g., the one or more sensors 104 such as a zone microphone), and isolates e.g., auditory cough characteristics from the received e.g., audio data (e.g., respiratory noises, oratory noises, etc.). Then the flow chart proceeds to 480-482.

At 480, the risk evaluator 160 determines the frequency of the cough. At 481, the risk evaluator 160 determines the approximate location of the cough in the audio. At 482, the risk evaluator 160 determines the characteristics of the cough. The frequency, location, and the characteristics of the cough can be used to differentiate the cough from respiratory noises, oratory noises, etc., and/or determine, e.g., a specific illness associated with the cough, the severity of the illness with the cough, whether the person coughing is ill, etc. Then the flow chart proceeds to 440.

At 440, the risk evaluator 160 conducts a risk evaluation, and determine a risk assessment (that includes a risk index represented by, e.g., integers from 1 to 10 or from 1 to 100, or a number between 0 and 1) indicative of e.g., the degree of the risk of spread virus, etc. at a certain location/area/zone for a given period of time. The risk assessment can be used to determine e.g., whether/which mitigation control is to be configured for the HVACR system 151. Then the flow chart proceeds to 450. It will be appreciated that the risk can decay overtime (e.g., three minutes after a person's coughing), and the changes of the risk assessment overtime can be indicative of the types of the risk.

At 450, the risk evaluator 160 (or a processor or a controller) compares the risk assessment with a predetermined threshold (e.g., a maximum threshold). If the risk assessment is greater than the maximum threshold, the flow chart proceeds to 460 where an alert is raised by the risk evaluator 160 (or a processor or a controller). If the risk assessment is equal to or less than the maximum threshold, the risk assessment is compared with a second predetermined threshold. If the risk assessment is equal to or less than the second predetermined threshold, no action would be taken (or a default/predetermined configuration is to be chosen). If the risk assessment is greater than the second predetermined threshold, the flow chart proceeds to C. It will be appreciated that the second predetermined threshold can be compared with the risk assessment before the risk assessment is compared with the maximum threshold.

Figure 5:
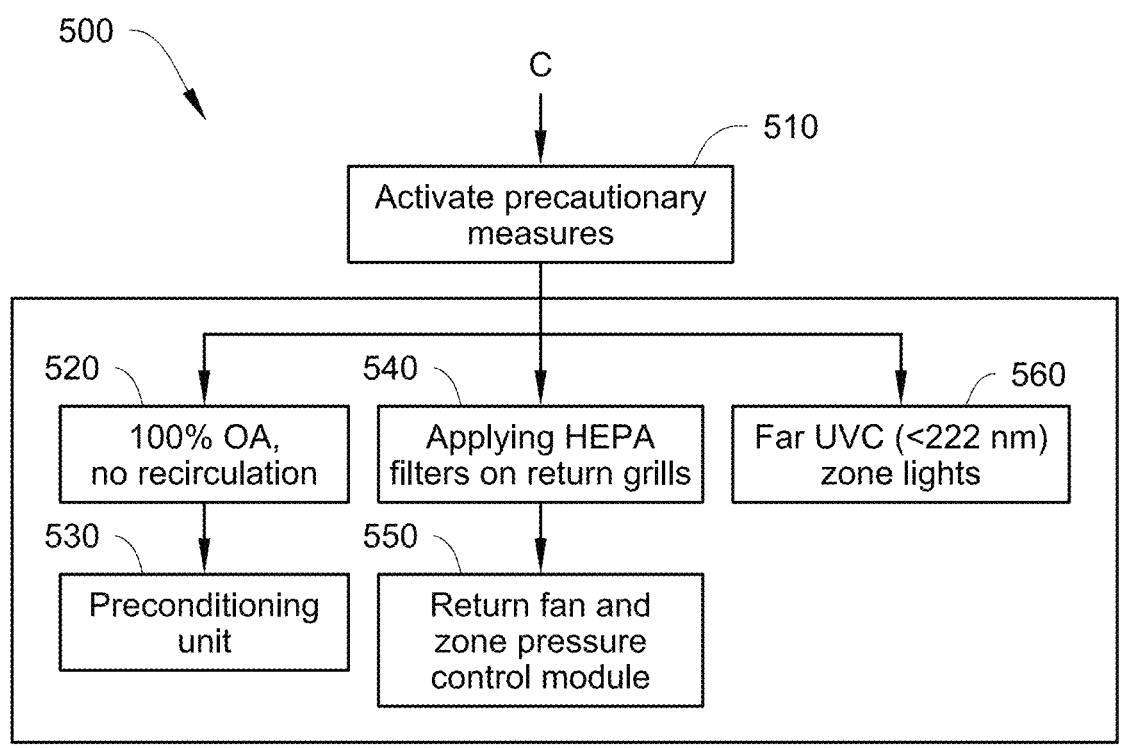
FIG. 5 illustrates a flow chart of controls of a BMS (or a processor or a controller) of an IAQ analytics, simulation, and control system, according to an embodiment.

FIG. 5 illustrates a flow chart 500 of controls of a BMS 130 (or a processor or a controller) of an IAQ analytics, simulation, and control system, according to one embodiment. The flow chart 400 starts from 510. At 410, the BMS activate precautionary measures based on the risk assessment from C. Then the flow chart proceeds to 520, 540, or 560 based on the risk assessment.

At 520, the risk assessment is at level one (e.g., exceeds a threshold but within a first range, e.g., from 0 to 0.2), and the BMS 130 is configured to operate the HVACR system with a first configuration (e.g., 100% outdoor air, no recirculation, etc.). Then the flow chart proceeds to 530. At 530, a preconditioning unit of the BMS 130 is operated.

At 540, the risk assessment is at level two (e.g., exceeds the threshold but within a second range higher than the first range, e.g., from >0.2 to 0.4), and the BMS 130 is configured to operate the HVACR system with a second configuration (e.g., applying High Efficiency Particulate Air (HEPA) filters on return grills). Then the flow chart proceeds to 550. At 550, a return fan and/or a zone pressure control module of the BMS 130 is operated.

At 560, the risk assessment is at level three (e.g., exceeds the threshold but within a third range higher than the second range, e.g., from >0.4 to 0.6), and the BMS 130 is configured to operate the HVACR system with a third configuration (e.g., operating far UVC (<222 nm) zone lights).

Figure 6:
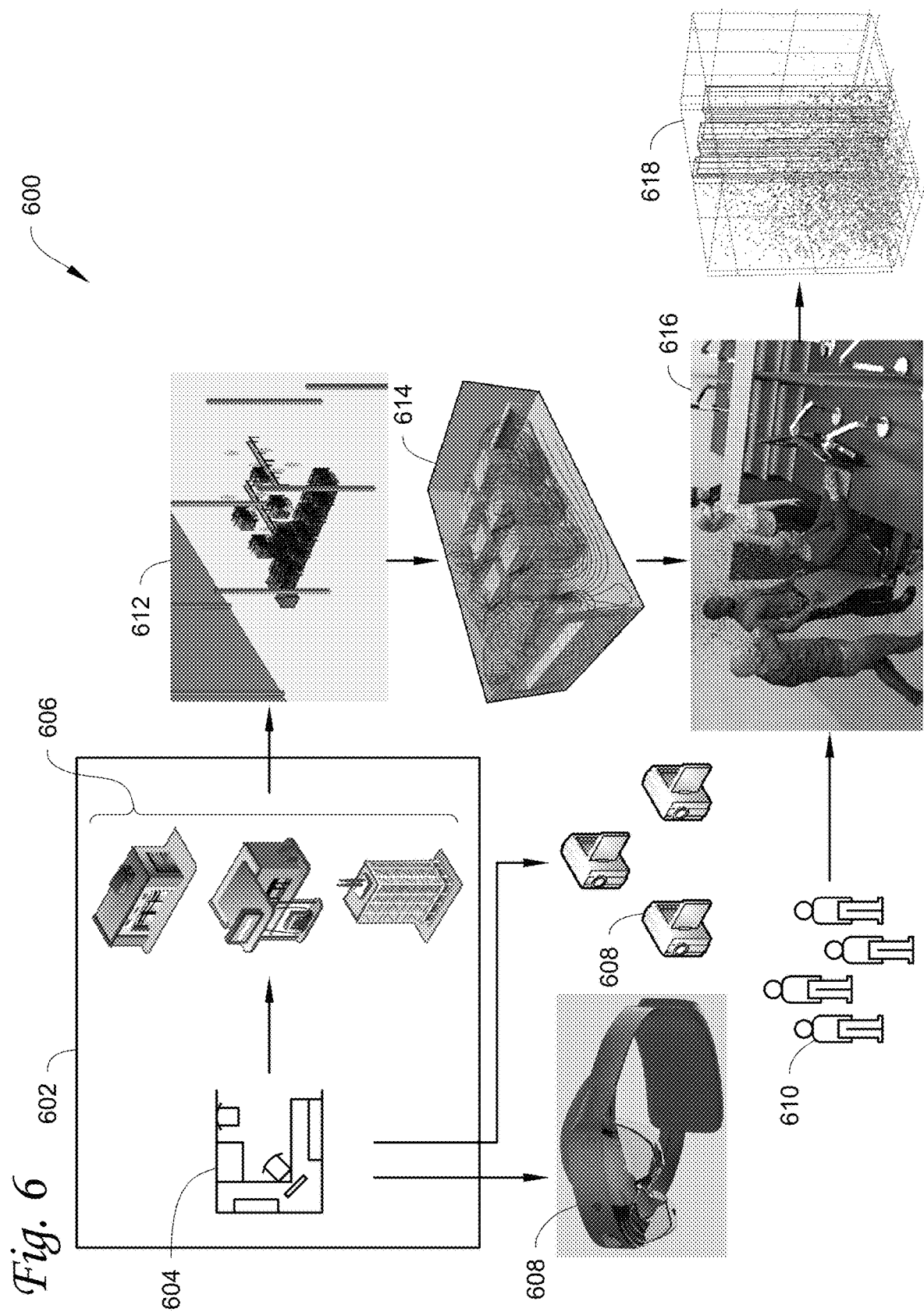
FIG. 6 shows an information workflow for modeling indoor air quality according to an embodiment.

FIG. 6 shows an information workflow for modeling indoor air quality according to an embodiment. The information workflow 600 includes obtaining a model of the space 602. The model of the space can be obtained at 602 by, for example, use of two-dimensional (2-D) plans 604, three-dimensional (3-D) plans 606, or captures of the space using, for example, wearable or portable cameras 608. Movement of persons is obtained at 610. Airflow into the space is modeled 612. Airflow through the space is modeled 614. The spread risk of a virus within the space is modeled 616. The effects of an air purifier on the spread risk of the virus can be modeled 618.

Model of space 602 is a model of the structures in place within the space that can affect airflow in said space. The structures can include, for example, walls, pillars, doors, the open/closed state of doors, location of ducts and vents, windows, the state of windows, and the like. The model of the space 602 can be obtained from one or more sources, such as 2-D plans 604, 3-D plans 606, or various devices, such as cameras 608. 2-D plans 604 can be, for example, floorplans for the building or other such 2-D representations of the space. 3-D plans can be representations of the space in three dimensions, such as architectural plans, CAD diagrams, 3-D maps of the space, or the like. In an embodiment, cameras 608 can be used to generate a map of the space by capturing image data that is aggregated and optionally combined with movement and/or position data for the cameras 608 at the time of imaging to generate a model of the space 602. The cameras can be included in, for example, wearable devices such as smart glasses, smart watches, or smart phones, or any other suitable device that may be moved through the space and in position to capture images thereof.

Movement of persons 610 can be incorporated into the model of the space. The movement of persons 610 can be captured for incorporation into the model by, for example, cell phones or wearable devices tracking their respective users' positions (which can optionally be anonymized), sensors within the zones such as cameras, or other such suitable devices for identifying the positions of persons within the space and changes in those positions over time.

The movement of persons 610 can be used, for example, to model actual risk of viral transmissions among persons based on, for example, proximity of the persons, durations within such proximities, locations of the persons, locations where the persons are in particular proximities to one another, and the like. This can allow the model to represent the risks of viral transmission to or among the persons in the space with greater fidelity, accounting for the actual positions within the space where there may be contact. The movement of persons within the space 610 can include the pathways taken by the persons in the space, interactions among persons in the space, dwell time in certain areas within the space, or any other suitable data on the locations of persons within the space and changes in such over time.

Airflow entering the space 612 can be modeled based on, for example, the model of the space 602, identifying locations where airflow is introduced to the space and the characteristics of those airflows, using modeling of the various ducts and outlets of an HVACR system, the position and state of windows and exterior doors or doors connecting to other spaces, conditions in the ambient environment, and other information representative of such sources of air entering the space or their respective statuses. The modeling of airflow entering the space 612 can be based on any suitable modeling techniques for such flows, for example, computational fluid dynamics (CFD) models of the airflow that would be provided by the sources under the given conditions.

Airflow through the space 614 can then be modeled from the model of the space 602 and the model of the airflow into the space 612. The modeling of the airflow through the space can be any suitable modeling of flows, for example CFD models of airflow. The modeling of airflow through the space can, for example, indicate low air movement zones with stagnant air, model local temperature and/or humidity differences, express the direction of airflow through the space with respect to various persons within the space and provide other such information regarding conditions within the space relevant to the risk of spread of a virus 616.

Risk of spread of a virus 616 can be modeled from the various parameters collected in information workflow 600 including the models of the movement of persons within the space 610, the model of airflow into the space 612, and the model of airflow through the space 614. The risk of spread of a virus 616 can be based on the air quality conditions at the particular locations where persons are in proximity based on their movement within the space obtained at 610, along with the number or duration of contacts. In an embodiment, modeling the risk of spread of a virus 616 can be based on particular persons in the space identified as potential viral carriers, for example, due to observed behaviors such as coughs or health data such as contact tracing or other health data described below, and movement of those persons in the space as obtained at 610, along with airflows around the positions of these persons. In an embodiment, risk of spread of a virus can include modeling of particulate spread from a cough, or other potential source of virus particles. The modeling of the risk of spread of a virus 616 can use CFD analysis to project the travel of the virus particles, for example based on airflow through the space modeled at 614. In an embodiment, modeling the risk of spread of a virus 616 can be performed in response to a detected virus spreading event, such as a cough.

The risk of spread of a virus modeled at 616 can further be based on health data indicative of the likelihood of spread or risk presented by infection of the persons within the space. The health data can include demographic data, such as the sex or age of the persons within the space. The health data can include health parameters of the person such as prior conditions or potential indicators of susceptibility to illness such as, for example, blood type or genetic predispositions observed for particular diseases such as, for example, COVID-19. The health data can be associated with persons within the space based on identifiers, such as worker identification badges or other methods of determining presence of a particular person and associating the particular person with the health data. The health data can include contact tracing data, for example, contact tracing data captured by cell phones, contact tracing data derived from other health data and the movement of persons within the space obtained at 610, or any other suitable source of contact tracing data for persons within the space. The health data can be combined with observations of behavior such as the video analysis described above to determine a likelihood that one or more of the persons within the space may present an infection risk. The observations of behavior can be used in developing contact tracing data for persons within the space.

Effects of the air purifier 618 can also be modeled. Air purifiers can include, for example, UV disinfection of air, filtration such as HEPA filters, sources of radicals capable of inactivating pathogens such as, for example, dry hydrogen peroxide, sources of ozone, or the like. Air purifiers modeled at 618 can be, for example, incorporated into building systems such as HVACR systems, one or more units that may be placed within the space, combinations thereof, or any other configuration of air purifiers. Air purifiers modeled at 618 can have one or more operational modes in which they provide air purification. Intake and outlet of purified air by each air purifier and particular operational characteristics of the air purifiers, such as quantity of radicals and their diffusion into the space, extent of pathogen inactivation by UV light, and the like can be modeled when modeling the effects of the air purifier at 618. The modeling of the effects of the air purifiers can further be modeled for each of multiple operating modes for air purifiers having multiple modes. Further, the effects of the air purifiers can be modeled for potential locations within the space for air purifiers that are units within the space, based, for example, on the models of airflow through the space from 614 or tracking of flows including virus particles, which can be modeled as part of the risk of spread of the virus in 616. The effects of air purifiers modeled at 618 can be used, for example, to identify locations maximizing impact of air purifiers in reducing risk of spread of a virus as modeled in 616. In an embodiment, the effects of air purifiers modeled at 618 can be used to determine the extent to which risk can be mitigated, for example to inform a decision whether to use risk mitigation or to issue an alert, such as at decision point 450 in FIG. 4.

The model of air quality generated using workflow 600 can be used, for example, as simulator 120 shown in FIG. 1 and described above. The model of air quality can be used as an element in determining a risk of spread of a virus, and further for determining the possible remedial actions and their effects on reducing such risk, such as the available resources for risk mitigation (HVACR systems, other air purifiers, points of ventilation, local controls within said space, and the like) and further to predict their effects by modeling the conditions when operating under the potential risk mitigation mode (i.e. airflows when ventilation is increased, effectiveness of particular locations or activities of air purifiers, and the like).

The model of air quality generated using workflow 600 can be updated dynamically, for example to reflect changes in the movement of persons through the space 610, changes to the layout within the space that could affect airflow through the space 614, changes in HVACR system settings, ventilation, or other conditions affecting the airflows entering the spaces, current positions and operation characteristics of any movable or controllable air purifiers, and the like. In an embodiment, the model of air quality is iterated prior to any determination of risk or determination of a mitigation action that may be based on the model of air quality. These dynamic updates can account for changes in behavior quickly, such as responses to policies regarding worker scheduling, social distancing or even ordinary changes to pathing within the space such as changes of positions of objects such as desk layouts, avoidance of areas where there have been spills or cleaning, and the like. Further, the model according to workflow 600 can include far more data points than typically incorporated into viral transmission models, improving the fidelity of the model.

Figure 7:
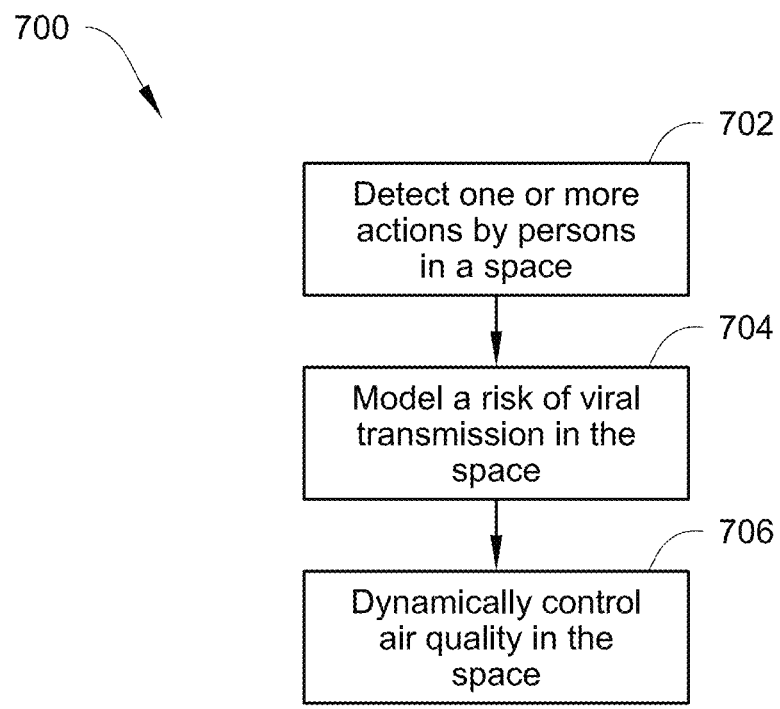
FIG. 7 shows a flowchart of a method of controlling indoor air quality according to an embodiment.

FIG. 7 shows a flowchart of a method of controlling indoor air quality according to an embodiment. Method 700 includes detecting one or more actions by one or more persons within a space 702, modeling a risk of viral transmission based on the detected one or more actions by the one or more persons within the space 704, and dynamically controlling air quality within the space 706.

One or more actions by one or more occupants of the space are detected 702. The one or more actions can include, for example, entering the space, moving through the space, position relative to other occupants of the space, actions indicative of illness such as having an elevated temperature. The actions can be detected by any suitable means for the selected one or more actions, for example, use of identification badges at entry to the space, location data from cell phones or wearable devices, observation of the space using sensors such as cameras, infrared cameras, microphones, or the like, and processing of such observation to detect the particular actions such as presence, movement, coughing or other illness indicators and the like.

Optionally, the one or more occupants can be identified as particular persons. The identification of the occupants can be used to associate the presence of the person with particular characteristics, such as the health data described above, such as demographic information, previous illnesses, preexisting conditions, genetic susceptibility data, contact tracing, or other such health data. Once the association is made, the particular persons may be anonymized, with only the associated characteristics, not the particular person themselves, being used in subsequent modeling of risk at 704 and control of air quality at 706. The identification of particular persons can be through, for example, an identification badge that is read on entry into the space, a cell phone or wearable device of the particular person, or the like. In an embodiment, a cell phone or wearable device of the particular person can transmit the health data directly without needing to supply an identification of the particular person.

A risk of viral transmission is modeled 704. The risk of viral transmission modeled at 704 can be based at least in part on one or more of the proximity of occupants, the locations where occupants are in proximity, air quality at the particular locations where occupants are in proximity, and the like. The air quality at the locations can be based on, for example, temperature of the air, humidity of the air, measures of ventilation such as the amount of fresh air from outside the space that reaches the location, and the like. The risk determined at 704 can account for the one or more actions detected at 702, for example including estimates of the likelihood of one or more occupants being infected, an amount of potential viral particulate due to number and intensity of coughs, or the like. The risk of viral transmission modeled at 704 can be the risk of spread of a virus modeled at 616 according to information workflow 600 described above and shown in FIG. 6. The risk of viral transmission can optionally be adjusted based on health data of occupants such as that described above, including, for example, data indicative of susceptibility to viruses, such as demographic factors, prior or preexisting conditions, or genetic indicators of susceptibility to viruses.

Air quality in the space is dynamically controlled 706. The dynamic control of air quality can include controlling one or more of temperature within the space, humidity within the space, ventilation of the space, or operation of an air cleaner within the space based on the risk of viral transmission within the space modeled at 704. Operation of an air cleaner can include the operational mode of the air cleaner and/or a position of the air cleaner for air cleaners that can be moved within the space. The dynamic control of air quality in the space can be to reduce the risk of viral transmission modeled at 704 towards a target value or below a threshold value. In an embodiment, the dynamic control of air quality at 706 can include satisfying the risk of viral transmission balanced with comfort or efficiency parameters such as temperature, humidity, amount of ventilation, and the like. The dynamic control of air quality can be achieved by controlling building systems, such as building mechanical systems 150 including an HVACR system 151, controlling the location and/or operating mode of one or more air cleaners such as air purifiers, or any other behavior affecting air quality. The variations in the parameters that can reduce a risk of viral transmission include elevating the temperature, elevating the humidity, increasing a percentage of fresh air in ventilation, or improving the effectiveness of one or more air cleaners such as air purifiers. The improvement of the effectiveness of an air cleaner can include modifying an operating mode of the air cleaner, modifying a position of the air cleaner, or modifying airflow through the space including the air cleaner, for example by modifying airflow into the space. Whether a modification improves effectiveness of the air cleaner can be determined by modeling, for example using a model according to the information workflow 600 described above and shown in FIG. 6, particularly the effectiveness of an air cleaner modeled at 618, using the modeling to predict effectiveness at the operating mode, position, or airflow that may be adopted in the dynamic control at 706. The modeling used for such dynamic control can be dynamic modeling from at or near the point in time at which the dynamic control of 706 will take effect, for example modeling current conditions when assessing control actions to take. The dynamic control at 706 can be provided iteratively, continuously, according to a schedule, or event-based, such as being triggered by events such as changes to the risk of viral transmission modeled at 704.

Figure 8:
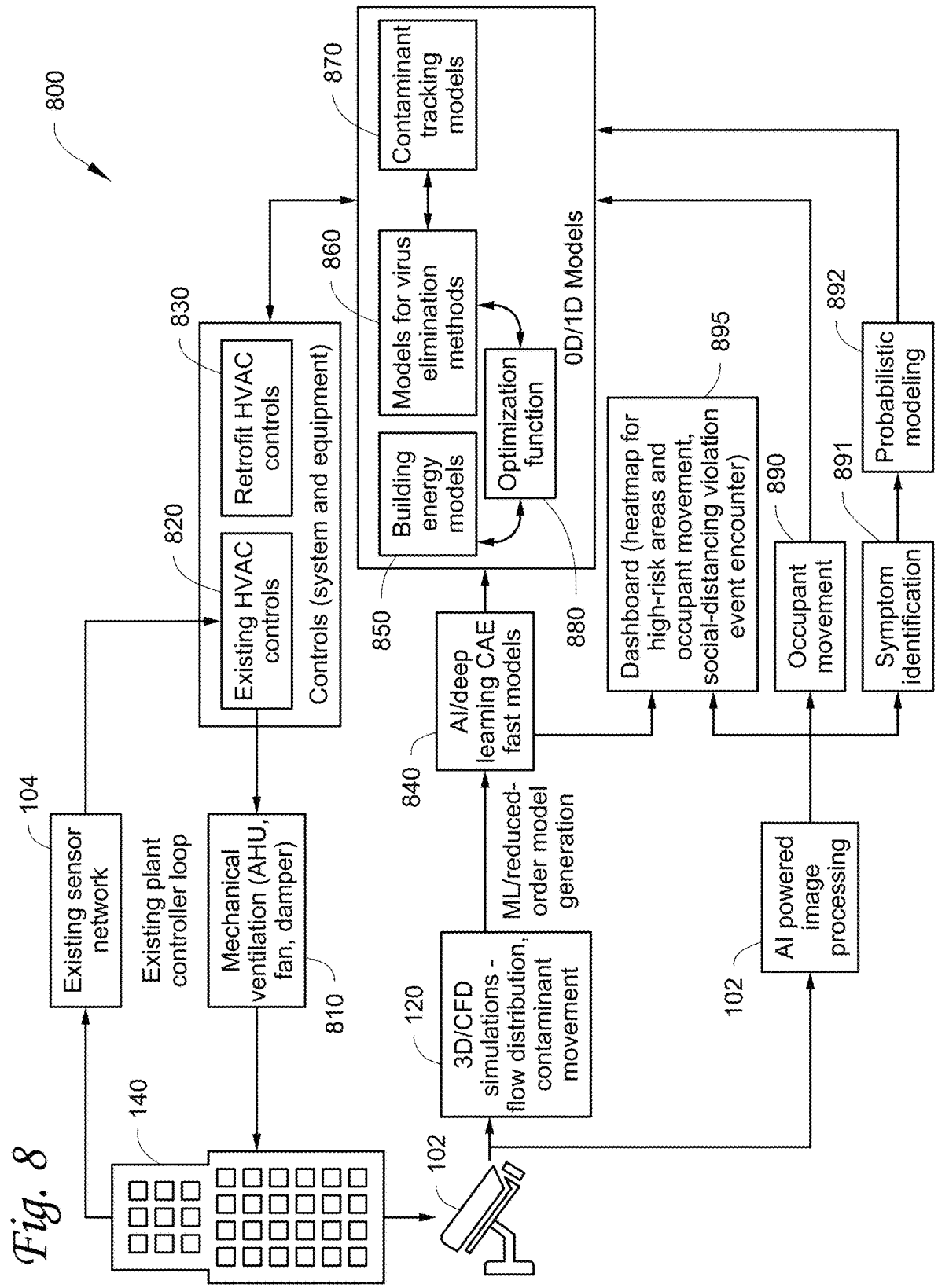
FIG. 8 illustrates a schematic view of an IAQ analytics, simulation, and control system, according to one embodiment.

FIG. 8 illustrates a schematic view of an IAQ analytics, simulation, and control system 800, according to one embodiment. The system includes a facility 140 (see FIG. 1), one or more cameras 101 (see FIG. 1), one or more sensors 104 (see FIG. 1), a simulator 120 (see FIG. 1), and one or more analytics modules 102 (see FIG. 1).

The one or more analytics modules 102 can include an image processing module to process the images generated from the video captured by the one or more cameras 101. In one embodiment, the image processing module can perform Artificial Intelligence (AI) powered image processing (e.g., image processing using AI and/or machine learning (ML) and/or Deep Leaning, etc.).

The one or more analytics modules 102 can determine the behavior parameters (e.g., occupant movement 890, disease symptom identification 891 including symptom characteristics, etc.) based on e.g., the video captured from the one or more cameras 101, the parameters obtained through the one or more wearable devices 103, and/or the data sensed/captured by the one or more sensors 104. A probabilistic modeling 892 can be run on the behavior parameters (e.g., disease symptom identification 891) obtained from the one or more analytics modules 102 to generate a probability of infected occupant's presence in the indoor space of the facility 140.

The simulator 120 can be configured to perform e.g., 3D and/or Computational Fluid Dynamics (CFD) modeling and/or simulations, to simulate e.g., airflow distribution, contaminant (bacteria, virus, or other pathogens, etc.) movement, etc., to determine e.g., the airflow stagnation zones and high airflow zones in the indoor space of the facility 140. The simulator can estimate the airflow distribution for given zone geometry and placement of air supply and/or return vents. The simulator can also track e.g., the coughing or sneezing of a person or persons to determine e.g., where the droplets move, due to the airflow simulation, and determine the critical points/paths.

The system 800 also includes a model generator 840. In one embodiment, the model generator 840 can be configured to generate AI and/or Deep Learning Computer Aided Engineering (CAE) fast models, using ML and/or reduced-order model generation technologies. It will be appreciated that the 3D/CFD models and/or results generated by the simulator 120 typically contains a large amount of data, and the cost and time of simulating the 3D/CFD models and/or results generated by the simulator 120 are very high. As such, a reduced-order model such as a zero dimension (0D) or one dimension (1D) model reflective of the results of the 3D/CFD model can be generated (using AI and/or Deep Learning CAE fast models or other methods) to save cost and/or time in subsequent processing.

The 0D and/or 1D models of the airflow (or contaminant movement) model generated from the model generator 840 can be fed into a control simulator (or "0D/1D module") (850, 860, 870, 880). The probability of infected occupant's presence in the indoor space of the facility 140 generated from the probabilistic modeling 892 can also be fed into the control simulator. Also the behavior parameters (e.g., occupant movement 890) can be fed into the control simulator.

In one embodiment, the occurrence of the above events (contaminant movement, occupant movement, etc.) and their characteristics, and/or the probability of infected occupant's presence from the probabilistic modeling 892 can be fed in the virus/contaminant tracking models 870 of the control simulator (850, 860, 870, 880).

The system 800 further includes controls (system and equipment) such as default HVACR controls 820 and retrofit HVACR controls 830. In one embodiment, the retrofit HVACR controls 830 are default HVACR controls 820 modified by feedback controller models (e.g., modified based on inputs from the sensor network 104, and/or modified based on the control models generated from the control simulator (850, 860, 870, 880), etc.).

Building energy models 850 can be models of energy consumption or efficiency based on controlled parameters such as temperature, humidity, operation of air cleaners, and the like. The building energy models can be used to determine energy consumption at particular operating parameters for building systems, such as energy consumption at particular temperatures, particular humidity values, particular amounts of fresh air being used, or by the operation of virus elimination methods such as energy to operate air cleaners, or their impact on energy consumption, such as added fan energy consumption by the use of filters, and the like. The models for virus elimination methods 860 can be generated by the control simulator based on the virus/contaminant tracking models 870. Models of virus elimination methods 860 model the effectiveness of particular methods of virus elimination. The models can be, for example, modeling of the effects of an air purifier 618 as described above and shown in FIG. 6. The models of virus elimination methods 860 can model the reduction in risk of viral transmission when one or more methods of mitigating transmission risk such as increasing temperature or humidity, increasing outside air ventilation, or operating or moving an air purifier.

The virus/contaminant tracking models 870 can be generated by using the 0D and/or 1D models such as the AI and/or Deep Learning CAE fast models from the model generator 840, the probability from the probabilistic modeling 892, and/or the behavior parameters (e.g., occupant movement 890). Models for tracking contaminants 870 can determine where contaminants are and how those locations may change under different virus elimination methods. Models for tracking contaminants 870 can combine with the models of virus elimination methods to further refine determination of the models effectiveness of virus elimination methods 860 and their reduction to the risk of virus transmission, for example by mapping the tracked contaminants to locations where persons are in contact within the space. The models for tracking contaminants can provide feedback loops to the models of virus elimination methods 860, or adjustments to weight the effectiveness modeled at 860 based on where contaminants are reduced or moved.

That is, the models for tracking contaminants 870 and the virus-elimination retrofit models (e.g., models 860 for retrofitted HVACR controls 830) can be co-simulated to estimate the extent of the measures (effectiveness, efficacy, etc.) for all types of models.

The control simulator (850, 860, 870, 880) uses building energy models 850 to simulate the building energy consumption and estimate the cost of such energy. The control simulator (850, 860, 870, 880) also uses models for virus elimination methods 860 to simulate the efficiency and safety of pathogen elimination. The two simulations are intertwined (e.g., each as a feedback to the other) to achieve an optimization function 880 (e.g., to achieve an optimal model that balance the effectiveness of the pathogen killing model and the cost-saving of the building energy consumption model associated with such pathogen killing model) based on, e.g., a predetermined user's requirement. Optimization functions 880 can be used to optimize for efficiency or mitigation of risk of viral transmission, or to optimize tradeoffs between those parameters, based on the building energy models 850 and the models of virus elimination methods 860. That is, the building energy models 850 and the virus-elimination retrofit models (e.g., models 860 for retrofitted HVACR controls 830 that represent virus elimination/containment measures), which are typically energy intensive if being deployed, can be co-simulated through the optimization function 880 to maintain an optimal/balanced safe indoor environment with minimal energy impact. E.g., the airflow quality control (e.g. pathogen elimination control) can be, e.g., continuous or during the time when the risk assessment exceeds a predetermined threshold; the location to apply the airflow quality control can be, e.g., on the entire building, on a particular zone (having terminal box and dedicated exhaust, etc.), or on determined critical points/paths.

The optimization functions can be, for example, machine learning algorithms, satisficing functions, mathematical models of one or both of efficiency and risk of viral transmission, or the like. In an embodiment, the optimization functions can select between different options for mitigation or the risk of viral transmission based on impact on energy consumption for those options. The options selected among may include multiple different possible operations for mitigation of the risk of viral transmission, such as controlling an HVACR system to increase temperature, increase humidity, incorporate more fresh outside air into the airflows into the space, or operate one or more air cleaners in particular modes, such as using filters such as HEPA filters in ducts, generating radicals such as dry hydrogen peroxide, irradiating air with UV radiation, or the like.

The control simulator (850, 860, 870, 880) can generate an optimal control containing building energy model with retrofit models that represent virus elimination/containment measures. The control by the control simulator can include operating modes for building controls such as HVACR systems, including existing HVACR systems 820 and retrofitted HVACR controls 830. These controls can further provide feedback to the zero- and one-dimensional models, such as data regarding particular operational modes, that can be used to further tune the models or provide current conditions which can be used the zero- and one-dimensional models to determine controls for the existing HVACR systems 820 and retrofitted HVACR controls 830. This in turn controls 810 (mechanical ventilation such as Air Handling Unit (AHU), fan(s), damper(s), etc.) in the facility 140.

Optionally, the system can further include dashboard 895. Dashboard 895 can collect, aggregate, and present the results of data and/or simulations such as those from AI/deep learning 840 or image processing 102 to users. The dashboard 895 can present the data to users on a display, controlled using a user interface. The users can be, for example, building management, health providers, or the like, or any person given access to view the data. The results of data and/or simulations can be processed to provide data in a form that can be viewed and understood by the users, such as, for example, heat maps for risk of viral transmission, high-traffic areas within the space, locations or numbers of incidents where social distancing policies have been violated, counts of events such as coughs or potential contacts where viral infection can spread. The dashboard 895 can show the user real-time data, for example heat maps for risk or traffic. In an embodiment, the dashboard can provide reports or other aggregations of data also including historical data, logs of events, or the like.

Embodiments disclosed herein can simulate energy intensive measures before deployment, co-simulated different pathogen killing models with energy models through optimization function to maintain safe indoor environment with minimal energy impact. Embodiments disclosed herein can also co-simulate the contaminant tracking models with the virus-elimination retrofit models to estimate the extent/effectiveness of measures. The control simulator (850, 860, 870, 880) can act as a virtual test-bench to test with the controls model.

Embodiments disclosed herein can enable trade off analysis of efficacy (e.g., effectiveness and safety of the people) of pathogen elimination and overall building energy consumption (e.g., costs and/or environment impact such as greenhouse gas output), to make a decision on optimal strategies that balance both efficacy and energy consumption requirements. Embodiments disclosed herein can also enable digital testing of control (of e.g., the HVACR system) strategies for safety and comfort using technologies such as 3D modeling, video surveillance, etc. Embodiments disclosed herein can further enable tracking of pathogen (bacteria, virus, etc.) contamination and heat maps of the indoor space, so as to determine the high risk areas (e.g., critical points/paths). Also embodiments disclosed herein can enable faster modeling via e.g., 0D/1D modeling, AI, etc., to determine the impact of various parameters and/or the changes to various parameters on e.g., energy consumption, efficacy of pathogen elimination, quality of the indoor air, etc. with low cost in a short period of time.

Aspects:

It is appreciated that any of aspects 1-13, 14-26, 27, 28-42, 43-51, 52-59, 60-75, and 76-93 can be combined with each other.

Aspect 1. An indoor air quality (IAQ) analytics and simulation system for a heating, ventilation, air conditioning, and Refrigeration (HVACR) system, comprising:
- an analytical recognition system; and
- an airflow simulator,
- wherein the analytical recognition system includes:
  - a video camera configured to capture a video sequence of an indoor space;
  - a video analytics module configured to perform video processing and analysis on the video sequence to:
    - identify one or more individuals by processing the video sequence of the indoor space;
    - determine behavior parameters for the one or more individuals based on the video sequence; and
    - generate non-video data for each of the behavior parameters,
- wherein the airflow simulator is configured to simulate an airflow of the indoor space based on the non-video data generated by the video analytics module.

Aspect 2. The analytics and simulation system of aspect 1, further comprising a controller, wherein the controller is configured to adjust control parameters of the HVACR system based on the simulated airflow of the indoor space.

Aspect 3. The analytics and simulation system of aspect 2, wherein the video processing and analysis on the video sequence, simulating the airflow of the indoor space based on the non-video data, and the controller adjusting the control parameters of the HVACR system are performed in real-time.

Aspect 4. The analytics and simulation system of any one of aspects 1-3, wherein the HVACR system is configured and deployed based on the simulated airflow of the indoor space.

Aspect 5. The analytics and simulation system of any one of aspects 1-4, wherein the behavior parameters include one or more of a distance among the one or more individuals, a facial direction of the one or more individuals, an object indicative of mask wearing of the one or more individuals, an action indicative of mask removing from the one or more individuals, a location of the one or more individuals, a movement of the one or more individuals, a velocity of the movement of the one or more individuals, a voice threshold of the one or more individuals, a body size of the one or more individuals, and a body temperature of the one or more individuals.

Aspect 6. The analytics and simulation system of any one of aspects 1-5, wherein the video analytics module is further configured to determine a rate of change for each of the behavior parameters, the rate of change for each of the behavior parameter is a change of the behavior parameter over a predetermined period of time.

Aspect 7. The analytics and simulation system of any one of aspects 1-6, wherein the airflow simulator is configured to create an airflow model using the non-video data as input, simulate the airflow in the indoor space, and determine a critical point based on the simulated airflow.

Aspect 8. The analytics and simulation system of aspect 7, further comprising a controller, wherein the controller is configured to adjust a control of the HVACR system on the airflow before the airflow reaches the critical point.

Aspect 9. The analytics and simulation system of aspect 7, further comprising a controller, wherein the controller is configured to place a pathogen killing device in the indoor space at or around the critical point.

Aspect 10. The analytics and simulation system of aspect 7, further comprising a controller, wherein the controller is configured to activate or deactivate control of a zone within the indoor space upstream of the critical point relative to a direction of the airflow.

Aspect 11. The analytics and simulation system of aspect 7, further comprising a controller, wherein the controller is configured to increase or decrease a pathogen killing material in the airflow upstream of the critical point relative to a direction of the airflow.

Aspect 12. The analytics and simulation system of any one of aspects 1-11, wherein the video sequence of the indoor space includes an audio and timestamps corresponding to the video sequence.

Aspect 13. The analytics and simulation system of any one of aspects 1-12, wherein the video camera is an infrared camera configured to capture a temperature of the one or more individuals.

Aspect 14. A method of analyzing and simulating indoor air quality (IAQ) for a heating, ventilation, air conditioning, and refrigeration (HVACR) system, comprising:
- obtaining a video sequence of an indoor space by a video camera;
- performing video processing and analysis on the video sequence by a video analytics module, wherein performing video processing and analysis includes:
  - identifying one or more individuals by processing the video sequence of the indoor space;
  - determining behavior parameters for the one or more individuals; and
  - generating non-video data for each of the behavior parameters based on the video sequence, and
- simulating an airflow of the indoor space by an airflow simulator based on the non-video data generated by the video analytics module.

Aspect 15. The method of aspect 14, further comprising adjusting control parameters of the HVACR system by a controller based on the simulated airflow of the indoor space.

Aspect 16. The method of aspect 15, wherein performing video processing and analysis on the video sequence, simulating the airflow of the indoor space based on the non-video data, and adjusting the control parameters of the HVACR system are performed in real-time.

Aspect 17. The method of any one of aspects 14-16, further comprising configuring and deploying the HVACR system based on the simulated airflow of the indoor space.

Aspect 18. The method of any one of aspects 14-17, wherein the behavior parameters include one or more of a distance among the one or more individuals, a facial direction of the one or more individuals, an object indicative of mask wearing of the one or more individuals, an action indicative of mask removing from the one or more individuals, a location of the one or more individuals, a movement of the one or more individuals, a velocity of the movement of the one or more individuals, a voice threshold of the one or more individuals, a body size of the one or more individuals, and a body temperature of the one or more individuals.

Aspect 19. The method of any one of aspects 14-18, further comprising determining a rate of change for each of behavior parameters, wherein the rate of change for each of the behavior parameter is a change of the behavior parameter over a predetermined period of time.

Aspect 20. The method of any one of aspects 14-19, further comprising:
  creating an airflow model using the non-video data as input by the airflow simulator;
  simulating the airflow in the indoor space; and
  determining a critical point based on the simulated airflow.

Aspect 21. The method of aspect 20, further comprising adjusting, by a controller, a control of the HVACR system on the airflow before the airflow reaches the critical point.

Aspect 22. The method of aspect 20, further comprising placing, by a controller, a pathogen killing device in the indoor space at or around the critical point.

Aspect 23. The method of aspect 20, further comprising activating or deactivating, by a controller, a control of a zone within the indoor space upstream of the critical point relative to a direction of the airflow.

Aspect 24. The method of aspect 20, further comprising increasing or decreasing, by a controller, a pathogen killing material in the airflow upstream of the critical point relative to a direction of the airflow.

Aspect 25. The method of any one of aspects 14-24, wherein the video sequence of the indoor space includes an audio and timestamps corresponding to the video sequence.

Aspect 26. The method of any one of aspects 14-25, wherein the video camera is an infrared camera configured to capture a temperature of the one or more individuals.

Aspect 27. An indoor air quality (IAQ) analytics and control system for a heating, ventilation, air conditioning, and refrigeration (HVACR) system, comprising:
  an analytical recognition system; and
  a controller,
  wherein the analytical recognition system includes:
  a video camera configured to capture a video sequence of an indoor space;
  a video analytics module configured to perform video processing and analysis on the video sequence to:
    identify one or more individuals by processing the video sequence of the indoor space;
    determine behavior parameters for the one or more individuals;
    determine a rate of change for each of the behavior parameters; and
    generate non-video data for the rate of change for each of the behavior parameters,
  wherein the controller is further configured to determine a risk assessment based on the data,
  wherein the controller is further configured to adjust control parameters of the HVACR system based on the risk assessment.

Aspect 28. An indoor air quality (IAQ) analytics and control system for a heating, ventilation, air conditioning, and refrigeration (HVACR) system, comprising:
  an analytical recognition system having a risk evaluator; and
  a controller,
  wherein the analytical recognition system is configured to capture and determine behavior parameters for one or more individuals in an indoor space,
  the risk evaluator is configured to determine a risk assessment based on the behavior parameters,
  the controller is configured to adjust control parameters of the HVACR system based on the risk assessment.

Aspect 29. The analytics and control system of aspect 28, wherein the analytical recognition system includes one or more wearable devices and one or more sensors, the one or more wearable devices and the one or more sensors are configured to capture the behavior parameters for the one or more individuals.

Aspect 30. The analytics and control system of aspect 28 or aspect 29, wherein the analytical recognition system includes:
  a video camera configured to capture a video sequence of the indoor space; and
  a video analytics module configured to perform video processing and analysis on the video sequence to:
    identify the one or more individuals by processing the video sequence of the indoor space; and
    determine the behavior parameters for the one or more individuals.

Aspect 31. The analytics and control system of aspect 30, wherein the video sequence of the indoor space includes an audio and timestamps corresponding to the video sequence.

Aspect 32. The analytics and control system of aspect 30, wherein the video camera is an infrared camera configured to capture a temperature of the one or more individuals.

Aspect 33. The analytics and control system of aspect 30, wherein the video analytics module is further configured to determine a rate of change for each of the behavior parameters, the rate of change for each of the behavior parameter is a change of the behavior parameter over a predetermined period of time.

Aspect 34. The analytics and control system of any one of aspects 28-33, wherein capturing and determining the behavior parameters, determining the risk assessment, and adjusting the control parameters of the HVACR system are conducted in real time.

Aspect 35. The analytics and control system of any one of aspects 28-34, wherein when the risk assessment exceeds a predetermined minimum threshold, the controller is configured to adjust the control parameters of the HVACR system.

Aspect 36. The analytics and control system of aspect 35, wherein when the risk assessment exceeds a predetermined maximum threshold, the controller is configured to issue an alert.

Aspect 37. The analytics and control system of any one of aspects 28-36, wherein the behavior parameters include one or more of a distance among the one or more individuals, a facial direction of the one or more individuals, an object indicative of mask wearing of the one or more individuals, an action indicative of mask removing from the one or more individuals, a location of the one or more individuals, a movement of the one or more individuals, a velocity of the movement of the one or more individuals, a voice threshold of the one or more individuals, a body size of the one or more individuals, and a body temperature of the one or more individuals.

Aspect 38. The analytics and control system of any one of aspects 28-37, wherein the analytical recognition system is configured to determine a critical point of an airflow for the risk assessment.

Aspect 39. The analytics and control system of aspect 38, wherein the controller is configured to adjust a control of the HVACR system on the airflow before the airflow reaches the critical point.

Aspect 40. The analytics and control system of aspect 38, wherein the controller is configured to place a pathogen killing device in the indoor space at or around the critical point.

Aspect 41. The analytics and control system of aspect 38, wherein the controller is configured to activate or deactivate control of a zone within the indoor space upstream of the critical point relative to a direction of the airflow.

Aspect 42. The analytics and control system of aspect 38, wherein the controller is configured to increase or decrease a pathogen killing material in the airflow upstream of the critical point relative to a direction of the airflow.

Aspect 43. A method of controlling indoor air quality, comprising:
detecting one or more actions by one or more persons within a space;
modeling a risk of viral transmission based on the detected one or more actions by the one or more persons within the space; and
dynamically controlling one or more of temperature within the space, humidity within the space, ventilation of the space, or operation of an air cleaner within the space based on the risk of viral transmission within the space.

Aspect 44. The method of aspect 43, wherein the one or more actions include entry into the space by a particular person, the method further includes obtaining health data for the particular person, and controlling the one or more of the temperature, the humidity, the ventilation, or the operation of the air cleaner is further based on the health data.

Aspect 45. The method of aspect 44, wherein the health data includes one or more of age, sex, contact tracing data, or blood type data.

Aspect 46. The method of any one of aspects 43-45, wherein when the one or more actions is associated with an increased viral risk the dynamic controlling includes one or more of increasing the temperature within the space, increasing the humidity within the space, adjusting the ventilation of the space by providing an increased quantity of fresh air, or operating the air cleaner at an increased level.

Aspect 47. The method of aspect 46, wherein the one or more actions associated with an increased viral risk include one or more of a cough exhibited by at least one of the one or more persons, an elevated body temperature in at least one of the one or more persons, absence or removal of a facial covering by at least one of the one or more persons.

Aspect 48. The method of any one of aspects 43-47, wherein the operation of the air cleaner includes generation of a radical.

Aspect 49. The method of aspect 48, wherein the generation of the radical includes providing ultraviolet radiation.

Aspect 50. The method of aspect 48, wherein the radical is dry hydrogen peroxide.

Aspect 51. The method of any one of aspects 43-50, wherein detecting the one or more actions comprises monitoring at least a portion of the space using one or more cameras configured to record video.

Aspect 52. A system for controlling indoor air quality, comprising:
one or more sensors configured to detect actions of one or more persons in a space;
a processor configured to receive information from the one or more sensors and determine one or more of a target temperature, a target humidity, a target amount of ventilation, or an operation of an air cleaner; and
an environmental control system configured to adjust one or more of a temperature of the space towards the target temperature, a humidity of the space towards the target humidity, an amount of ventilation towards the target amount of ventilation, or to operate the air cleaner according to the determined operation of the air cleaner.

Aspect 53. The system of aspect 52, wherein the action the one or more sensors are configured to detect include entry into the space of a particular person, and the processor is configured to receive health data of the particular person and determine the one or more of the target temperature, the target humidity, the target amount of ventilation, or the operation of an air cleaner further based on the health information.

Aspect 54. The system of aspect 53, wherein the health data includes one or more of age, sex, contact tracing data, or blood type data.

Aspect 55. The system of any one of aspects 52-54, wherein when the one or more actions include an action associated with an increased viral risk, the target temperature is higher than the temperature of the space, the target humidity is greater than the humidity of the space, the target amount of ventilation includes more fresh air than the amount of ventilation of the space, or the determined operation Aspect 56. The system of any one of aspects 52-55, wherein the air cleaner is configured to produce a radical.

Aspect 57. The system of aspect 56, wherein the air cleaner includes an ultraviolet (UV) light, and is configured to produces the radical using the UV light.

Aspect 58. The system of aspect 57, wherein the radical is dry hydrogen peroxide.

Aspect 59. The system of any one of aspects 52-58, wherein the one or more sensors include one or more cameras, and further including a processor configured to analyze video data from the one or more cameras to determine the one or more actions by persons in the space.

Aspect 60. An indoor air quality (IAQ) analytics and modelling system for a heating, ventilation, air conditioning, and refrigeration (HVACR) system, comprising:
an analytical recognition system; and
a model generator,
wherein the analytical recognition system is configured to capture and determine behavior parameters for one or more individuals in an indoor space,
the analytical recognition system is further configured to capture and determine spatial parameters of one or more objects in the indoor space,
the model generator is configured to generate a model based on the behavior parameters and the spatial parameters.

Aspect 61. The analytics and modelling system of aspect 60, wherein the model includes one or more of an airflow model modelling an airflow within the indoor space, a layout model modeling a spatial layout of the indoor space, an energy consumption model modeling an energy usage of the indoor space, a probability model modelling a risk of presence of infected individuals in the indoor space, an movement model modeling a movement of the one or more individuals in the indoor space, a contaminant tracking model modeling a movement of the infected individuals in the indoor space, and a pathogen elimination model modelling an effectiveness of pathogen elimination methods.

Aspect 62. The analytics and modelling system of aspect 60 or aspect 61, wherein the one or more objects in the indoor space include one or more of moving non-human objects, stationary non-human objects, and moveable non-human objects.

Aspect 63. The analytics and modelling system of any one of aspects 60-62, wherein the moving non-human objects include a forklift.

Aspect 64. The analytics and modelling system of any one of aspects 60-63, wherein the spatial parameters include one or more of a shape of an object, a size of the object, a length of the object, a width of the object, a height of the object, a volume of the object, a profile of the object, a geometry of the object, a location of the object, a gap between objects, and a velocity of a moving object.

Aspect 65. The analytics and modelling system of any one of aspects 60-64, wherein the analytical recognition system includes one or more wearable devices and one or more sensors, the one or more wearable devices and the one or more sensors are configured to capture the behavior parameters for the one or more individuals and/or the spatial parameters of the one or more objects in the indoor space.

Aspect 66. The analytics and modelling system of any one of aspects 60-65, wherein the analytical recognition system includes:
   a video camera configured to capture a video sequence of the indoor space; and
   a video analytics module configured to perform video processing and analysis on the video sequence to:
      identify the one or more individuals by processing the video sequence of the indoor space;
      identify the one or more objects by processing the video sequence of the indoor space;
      determine the behavior parameters for the one or more individuals; and
      determine the spatial parameters for the one or more objects.

Aspect 67. The analytics and modelling system of aspect 66, wherein the video sequence of the indoor space includes an audio and timestamps corresponding to the video sequence.

Aspect 68. The analytics and modelling system of aspect 66, wherein the video camera is an infrared camera configured to capture a temperature of the one or more individuals.

Aspect 69. The analytics and modelling system of aspect 66, wherein the video analytics module is further configured to determine a rate of change for each of the behavior parameters, the rate of change for each of the behavior parameter is a change of the behavior parameter over a predetermined period of time.

Aspect 70. The analytics and modelling system of aspect 66, wherein the video analytics module is further configured to determine a rate of change for each of the spatial parameters, the rate of change for each of the spatial parameter is a change of the spatial parameter over a predetermined period of time.

Aspect 71. The analytics and modelling system of any one of aspects 60-70, wherein capturing and determining the behavior parameters, capturing and determining the spatial parameters, and generating the model based on the behavior parameters and the spatial parameters are conducted in real time.

Aspect 72. The analytics and modelling system of any one of aspects 60-71, wherein the behavior parameters include one or more of a distance among the one or more individuals, a facial direction of the one or more individuals, an object indicative of mask wearing of the one or more individuals, an action indicative of mask removing from the one or more individuals, a location of the one or more individuals, a movement of the one or more individuals, a velocity of the movement of the one or more individuals, a voice threshold of the one or more individuals, a body size of the one or more individuals, and a body temperature of the one or more individuals.

Aspect 73. The analytics and modelling system of any one of aspects 60-72, wherein the analytical recognition system is configured to determine a critical point of an airflow for the indoor space.

Aspect 74. The analytics and modelling system of any one of aspects 60-73, wherein the model includes a computational fluid dynamics model, the model generator is further configured to reduce an order of the computational fluid dynamics model.

Aspect 75. The analytics and modelling system of any one of aspects 60-74, wherein the model includes a 3D model, the model generator is further configured to reduce an order of the 3D model.

Aspect 76. An indoor air quality (IAQ) analytics and simulation system for a heating, ventilation, air conditioning, and refrigeration (HVACR) system, comprising:
   an analytical recognition system; and
   a simulator,
   wherein the analytical recognition system is configured to capture and determine behavior parameters for one or more individuals in an indoor space,
   the analytical recognition system is further configured to capture and determine spatial parameters of one or more objects in the indoor space,
   the simulator is configured to perform a simulation based on the behavior parameters and the spatial parameters.

Aspect 77. The analytics and simulation system of aspect 76, wherein the simulation is performed on a model, the model includes one or more of an airflow model modelling an airflow within the indoor space, a layout model modeling a spatial layout of the indoor space, an energy consumption model modeling an energy usage of the indoor space, a probability model modelling a risk of presence of infected individuals in the indoor space, an movement model modeling a movement of the one or more individuals in the indoor space, a contaminant tracking model modeling a movement of the infected individuals in the indoor space, and a pathogen elimination model modelling an effectiveness of pathogen elimination methods.

Aspect 78. The analytics and simulation system of aspect 76 or aspect 77, wherein the simulation is performed on at least two models, the at least two models include two or more of an airflow model modelling an airflow within the indoor space, a layout model modeling a spatial layout of the indoor space, an energy consumption model modeling an energy usage of the indoor space, a probability model modelling a risk of presence of infected individuals in the indoor space, an movement model modeling a movement of the one or more individuals in the indoor space, a contaminant tracking model modeling a movement of the infected individuals in the indoor space, and a pathogen elimination model modelling an effectiveness of pathogen elimination methods.

Aspect 79. The analytics and simulation system of aspect 78, wherein each of the at least two models includes a requirement, the simulator is further configured to determine a balanced requirement based on the requirement of each of the at least two models.

Aspect 80. The analytics and simulation system of any one of aspects 76-79, wherein the one or more objects in the indoor space include one or more of moving non-human objects, stationary non-human objects, and moveable non-human objects.

Aspect 81. The analytics and simulation system of any one of aspects 76-80, wherein the moving non-human objects include a forklift.

Aspect 82. The analytics and simulation system of any one of aspects 76-81, wherein the spatial parameters include one or more of a shape of an object, a size of the object, a length of the object, a width of the object, a height of the object, a volume of the object, a profile of the object, a location of the object, a geometry of the object, a gap between objects, and a velocity of a moving object.

Aspect 83. The analytics and simulation system of any one of aspects 76-82, wherein the analytical recognition system includes one or more wearable devices and one or more sensors, the one or more wearable devices and the one or more sensors are configured to capture the behavior parameters for the one or more individuals and/or the spatial parameters of the one or more objects in the indoor space.

Aspect 84. The analytics and simulation system of any one of aspects 76-83, wherein the analytical recognition system includes:
 a video camera configured to capture a video sequence of the indoor space; and
 a video analytics module configured to perform video processing and analysis on the video sequence to:
  identify the one or more individuals by processing the video sequence of the indoor space;
  identify the one or more objects by processing the video sequence of the indoor space;
  determine the behavior parameters for the one or more individuals; and
  determine the spatial parameters for the one or more objects.

Aspect 85. The analytics and simulation system of aspect 84, wherein the video sequence of the indoor space includes an audio and timestamps corresponding to the video sequence.

Aspect 86. The analytics and simulation system of aspect 84, wherein the video camera is an infrared camera configured to capture a temperature of the one or more individuals.

Aspect 87. The analytics and simulation system of aspect 84, wherein the video analytics module is further configured to determine a rate of change for each of the behavior parameters, the rate of change for each of the behavior parameter is a change of the behavior parameter over a predetermined period of time.

Aspect 88. The analytics and simulation system of aspect 84, wherein the video analytics module is further configured to determine a rate of change for each of the spatial parameters, the rate of change for each of the spatial parameter is a change of the spatial parameter over a predetermined period of time.

Aspect 89. The analytics and simulation system of any one of aspects 76-88, wherein capturing and determining the behavior parameters, capturing and determining the spatial parameters, and performing the simulation based on the behavior parameters and the spatial parameters are conducted in real time.

Aspect 90. The analytics and simulation system of any one of aspects 76-89, wherein the behavior parameters include one or more of a distance among the one or more individuals, a facial direction of the one or more individuals, an object indicative of mask wearing of the one or more individuals, an action indicative of mask removing from the one or more individuals, a location of the one or more individuals, a movement of the one or more individuals, a velocity of the movement of the one or more individuals, a voice threshold of the one or more individuals, a body size of the one or more individuals, and a body temperature of the one or more individuals.

Aspect 91. The analytics and simulation system of any one of aspects 76-90, wherein the analytical recognition system is configured to determine a critical point of an airflow for the indoor space.

Aspect 92. The analytics and simulation system of any one of aspects 76-91, wherein the simulation is performed on a model, the model includes a computational fluid dynamics model, and the simulator is further configured to perform the simulation on a reduced-order model of the computational fluid dynamics model.

Aspect 93. The analytics and simulation system of any one of aspects 76-92, wherein the simulation is performed on a model, the model includes a 3D model, and the simulator is further configured to perform the simulation on a reduced-order model of the 3D model.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

With regard to the preceding description, it is to be understood that changes may be made in detail, especially in matters of the construction materials employed and the shape, size, and arrangement of parts without departing from the scope of the present disclosure. This specification and the embodiments described are exemplary only, with the true scope and spirit of the disclosure being indicated by the claims that follow.

What is claimed is:

1. A method of modeling and simulating indoor air quality (IAQ) for a heating, ventilation, air conditioning, and refrigeration (HVACR) system, comprising:
 determining behavior parameters for one or more individuals in an indoor space;
 determining spatial parameters of one or more objects in the indoor space;
 generating a model based on the behavior parameters and the spatial parameters;
 determining a critical location of an airflow to disinfect the airflow for the indoor space;
 determining a risk assessment based on the behavior parameters, the risk assessment being indicative of a degree of a risk at a location for a period of time;
  wherein determining the risk assessment based on the behavior parameters includes either:
   (a) comparing a body temperature with a temperature baseline and comparing an oxygen saturation with an oxygen saturation threshold; or
   (b) isolating auditory characteristics from audio data; and determining a frequency, a location, and characteristics of the auditory characteristics;
 when the risk assessment exceeds a threshold and is within a first range, operating the HVACR system with a first configuration, wherein the first configuration is 100% outdoor air or no recirculation;
 when the risk assessment exceeds the threshold and is within a second range higher than the first range, operating the HVACR system with a second configuration, wherein the second configuration is applying high efficiency particulate air filters; and
 when the risk assessment exceeds the threshold and is within a third range higher than the second range, operating the HVACR system with a third configuration, wherein the third configuration is operating far ultraviolet-C zone lights.

2. The method of claim 1, further comprising:
 adjusting a control of the HVACR system on the airflow before the airflow reaches the critical location.

3. The method of claim 1, further comprising:
 running the generated model; and
 performing a simulation of the airflow based on running of the generated model.

4. The method of claim 3, further comprising:
 determining a balanced requirement based on requirements of at least two simulations, wherein the at least two simulations are performed on at least two models, respectively,
each of the at least two models includes a requirement, and
determining the balanced requirement is based on the requirement of each of the at least two models.

5. The method of claim 1, further comprising:
reducing an order of the model.

6. The method of claim 1, wherein the model includes one or more of an airflow model modelling an airflow within the indoor space, a layout model modeling a spatial layout of the indoor space, an energy consumption model modeling an energy usage of the indoor space, a probability model modelling a risk of presence of infected individuals in the indoor space, an movement model modeling a movement of the one or more individuals in the indoor space, a contaminant tracking model modeling a movement of the infected individuals in the indoor space, and a pathogen elimination model modelling an effectiveness of pathogen elimination methods.

7. The method of claim 1, wherein the one or more objects in the indoor space include one or more of moving non-human objects, stationary non-human objects, and moveable non-human objects.

8. The method of claim 1, wherein the spatial parameters include one or more of a shape of an object, a size of the object, a length of the object, a width of the object, a height of the object, a volume of the object, a profile of the object, a geometry of the object, a location of the object, a gap between objects, and a velocity of a moving object.

9. The method of claim 1, wherein the behavior parameters include one or more of a distance among the one or more individuals, a facial direction of the one or more individuals, an object indicative of mask wearing of the one or more individuals, an action indicative of mask removing from the one or more individuals, a location of the one or more individuals, a movement of the one or more individuals, a velocity of the movement of the one or more individuals, a voice threshold of the one or more individuals, a body size of the one or more individuals, and a body temperature of the one or more individuals.

10. The method of claim 1, wherein the model includes a computational fluid dynamics model, the method further comprising:
reducing an order of the computational fluid dynamics model.

11. The method of claim 1, wherein the model includes a 3D model, the method further comprising:
reducing an order of the 3D model.

12. The method of claim 1, further comprising:
issuing an alert when the risk assessment exceeds a predetermined threshold.

13. The method of claim 1, further comprising:
adjusting control parameters of the HVACR system based on the risk assessment.

14. An indoor air quality (IAQ) modelling and simulating system for a heating, ventilation, air conditioning, and refrigeration (HVACR) system, comprising:
a controller,
wherein the controller is configured to:
determine behavior parameters for one or more individuals in an indoor space;
determine spatial parameters of one or more objects in the indoor space;
generate a model based on the behavior parameters and the spatial parameters;
determine a critical location of an airflow to disinfect the airflow for the indoor space;
determine a risk assessment based on the behavior parameters, the risk assessment being indicative of a degree of a risk at a location for a period of time,
wherein determining the risk assessment based on the behavior parameters includes either:
(a) comparing a body temperature with a temperature baseline and comparing an oxygen saturation with an oxygen saturation threshold; or
(b) isolating auditory characteristics from audio data; and determining a frequency, a location, and characteristics of the auditory characteristics;
when the risk assessment exceeds a threshold and is within a first range, operate the HVACR system with a first configuration, wherein the first configuration is 100% outdoor air or no recirculation;
when the risk assessment exceeds the threshold and is within a second range higher than the first range, operate the HVACR system with a second configuration, wherein the second configuration is applying high efficiency particulate air filters; and
when the risk assessment exceeds the threshold and is within a third range higher than the second range, operate the HVACR system with a third configuration, wherein the third configuration is operating far ultraviolet-C zone lights.

15. The method of claim 1, wherein operating the HVACR system with the first configuration includes operating a preconditioning unit,
wherein operating the HVACR system with the second configuration includes operating a return fan and/or a zone pressure control module.

16. The method of claim 1, further comprising:
removing personal information from the behavior parameters using an anonymizer.

* * * * *